(12) United States Patent
Escary

(10) Patent No.: US 7,041,794 B2
(45) Date of Patent: May 9, 2006

(54) POLYNUCLEOTIDES AND POLYPEPTIDES OF THE ERYTHROPOIETIN GENE

(75) Inventor: Jean-Louis Escary, Le Chesnay (FR)

(73) Assignee: Genodyssee, (FR)

( * ) Notice: Subject to any disclaimer, the term of this patent is extended or adjusted under 35 U.S.C. 154(b) by 447 days.

(21) Appl. No.: 10/113,824

(22) Filed: Mar. 29, 2002

(65) Prior Publication Data

US 2003/0050269 A1 Mar. 13, 2003

Related U.S. Application Data

(60) Provisional application No. 60/358,598, filed on Feb. 21, 2002, provisional application No. 60/345,440, filed on Jan. 4, 2002, provisional application No. 60/343,163, filed on Dec. 21, 2001.

(30) Foreign Application Priority Data

Apr. 4, 2001 (FR) ................................ 01 04603

(51) Int. Cl.
C07K 14/00 (2006.01)
C07K 17/00 (2006.01)
A16K 38/00 (2006.01)

(52) U.S. Cl. ........................ 530/350; 530/395; 514/2
(58) Field of Classification Search ................ 530/350, 530/395

See application file for complete search history.

(56) References Cited

U.S. PATENT DOCUMENTS

| | | | |
|---|---|---|---|
| 4,414,150 A | 11/1983 | Goeddel | 260/112.5 |
| 4,615,974 A | 10/1986 | Kingsman et al. | 435/68 |
| 4,678,756 A | 7/1987 | Parks | 436/123 |
| 4,748,233 A | 5/1988 | Sloma | 530/351 |
| 4,751,287 A | 6/1988 | Berzin et al. | 530/351 |
| 4,780,530 A | 10/1988 | Teraoka et al. | 530/351 |
| 4,801,685 A | 1/1989 | Goeddel et al. | 530/351 |
| 4,810,645 A | 3/1989 | Goeddel et al. | 435/68 |
| 4,816,566 A | 3/1989 | DeChiara et al. | 530/351 |
| 4,820,638 A | 4/1989 | Swetly et al. | 435/68 |
| 4,885,166 A | 12/1989 | Meyer et al. | 424/85.7 |
| 4,917,887 A | 4/1990 | Hauptmann et al. | 424/85.7 |
| 5,723,125 A | 3/1998 | Chang et al. | 424/134.1 |
| 6,555,343 B1 * | 4/2003 | DeSauvage et al. | 435/69.1 |

| | | | |
|---|---|---|---|
| 2002/0037841 A1 | 3/2002 | Papadimitriou | 514/8 |

FOREIGN PATENT DOCUMENTS

| | | |
|---|---|---|
| EP | 0 032 134 A2 | 1/1981 |
| EP | 0 051 873 A2 | 11/1981 |
| EP | 0 062 971 A2 | 3/1982 |
| EP | 0 073 635 A2 | 8/1982 |
| EP | 0 128 467 A1 | 5/1984 |
| EP | 0 141 484 A2 | 6/1984 |
| EP | 0 194 006 A1 | 1/1986 |
| EP | 0 236 920 A2 | 3/1987 |
| EP | 0 553 494 A1 | 12/1992 |
| GB | 2 079 291 A | 7/1981 |
| WO | WO 83/02458 | 1/1983 |
| WO | WO 83/02459 | 1/1983 |
| WO | WO 83/04053 | 4/1983 |
| WO | WO9505465 * | 2/1995 |
| WO | WO 01/11056 A1 | 8/2000 |

OTHER PUBLICATIONS

Chem, Y et al. Structural role of amino acids 99-110 in recombinant erythropoietin. (1991), vol. 202, pp. 225-229.*
Lee, N., et al., "*Interferon-$\alpha_2$ Variants in the Human Genome*," Journal of Interferon and Cytokine Research 15:341-349 (1995). XP-001016231.
Kita, M., et al., "*Determination of Interferon-$\alpha_2$Allele Composition in the Geneomic DNA from Healthy Voulunteers and Leukemic Patients in Japan*," Journal of Interferon and Cytokine Research 17:135-140 (1997) XP-001016233.
Piehler, J., et al., "*Fast Transient Cytokine-Receptor Interactions Monitored in Real Time by Reflectometric Interference Spectroscopy*," Analytical Biochemistry 289, 173-186 (2001), XP-002185474.
Piehler, J., et al., "*Mutational and Structural Analysis of the Binding Interface Between Type 1 Interferons and their Receptor Ifnar2*," J. Mol. Biol. (1999) 294, 223-237, XP-002185475.

* cited by examiner

Primary Examiner—James Ketter
Assistant Examiner—Tara L. Garvey
(74) Attorney, Agent, or Firm—Mark A. Hofer; Brown Rudnick Berlack Israels LLP

(57) ABSTRACT

The present invention relates to new polynucleotides deriving from the nucleotide sequence of the EPO gene and comprising new SNPs, new polypeptides derived from the natural EPO protein and comprising at least one mutation caused by the SNPs of the invention as well as their therapeutic uses.

6 Claims, 7 Drawing Sheets

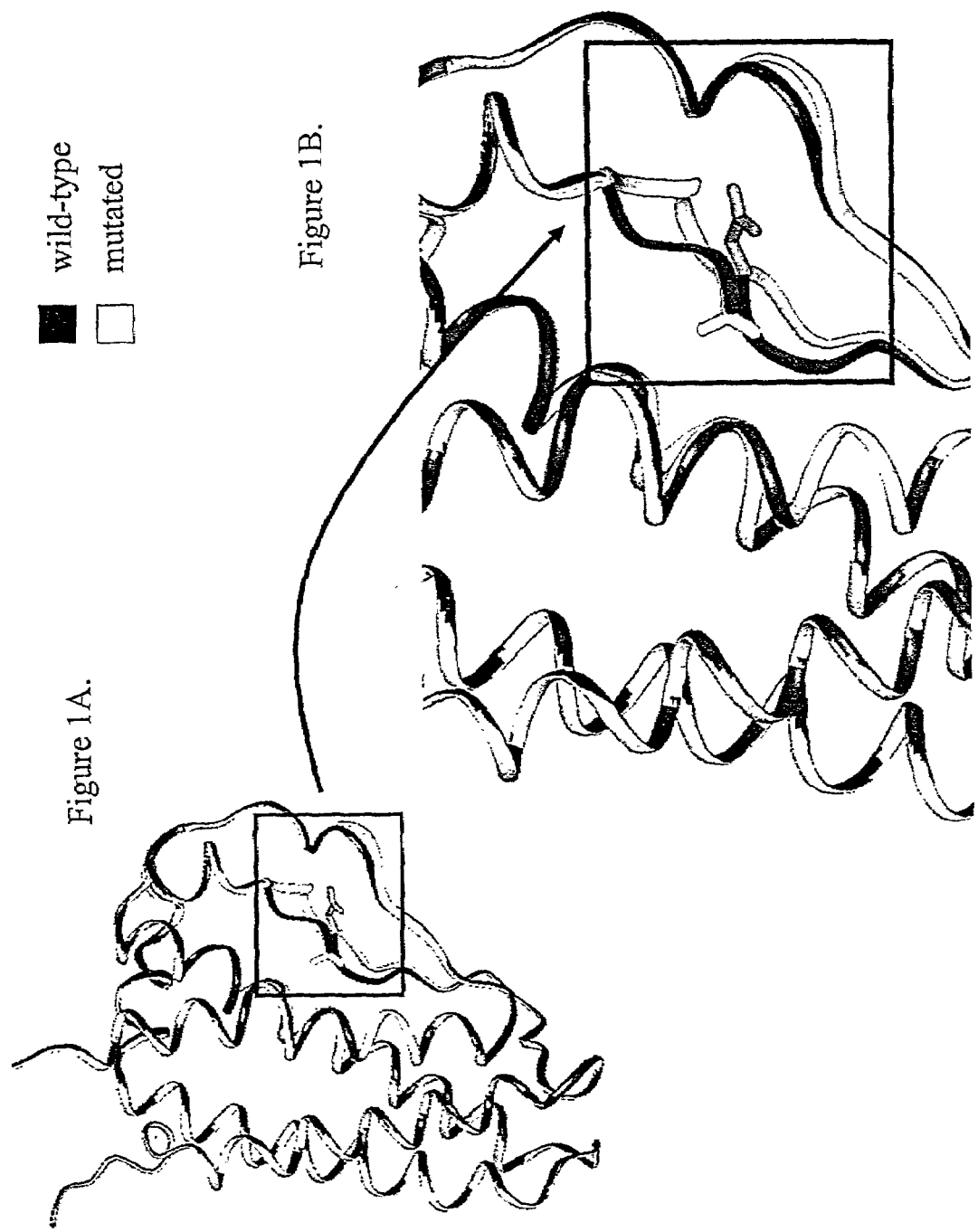

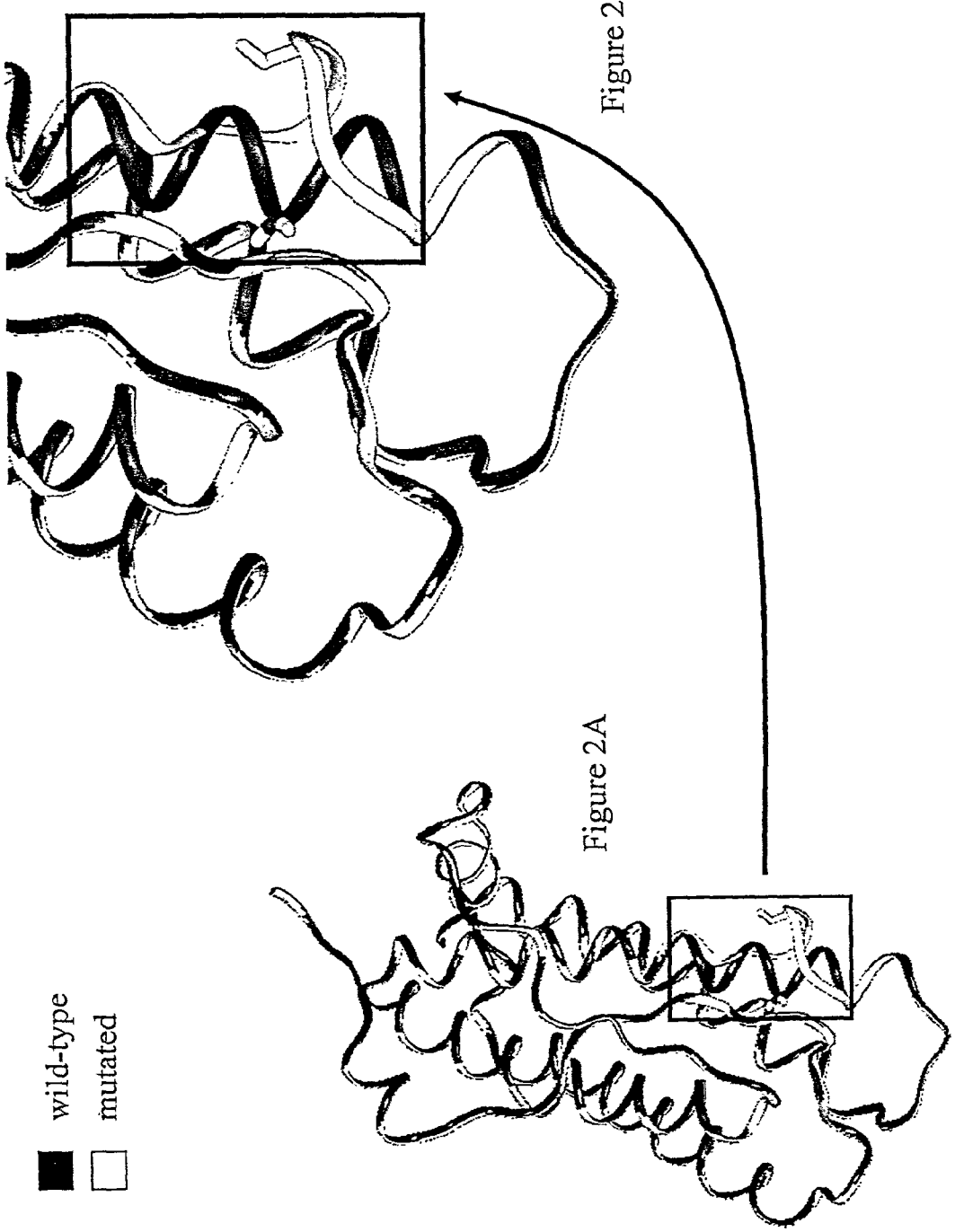

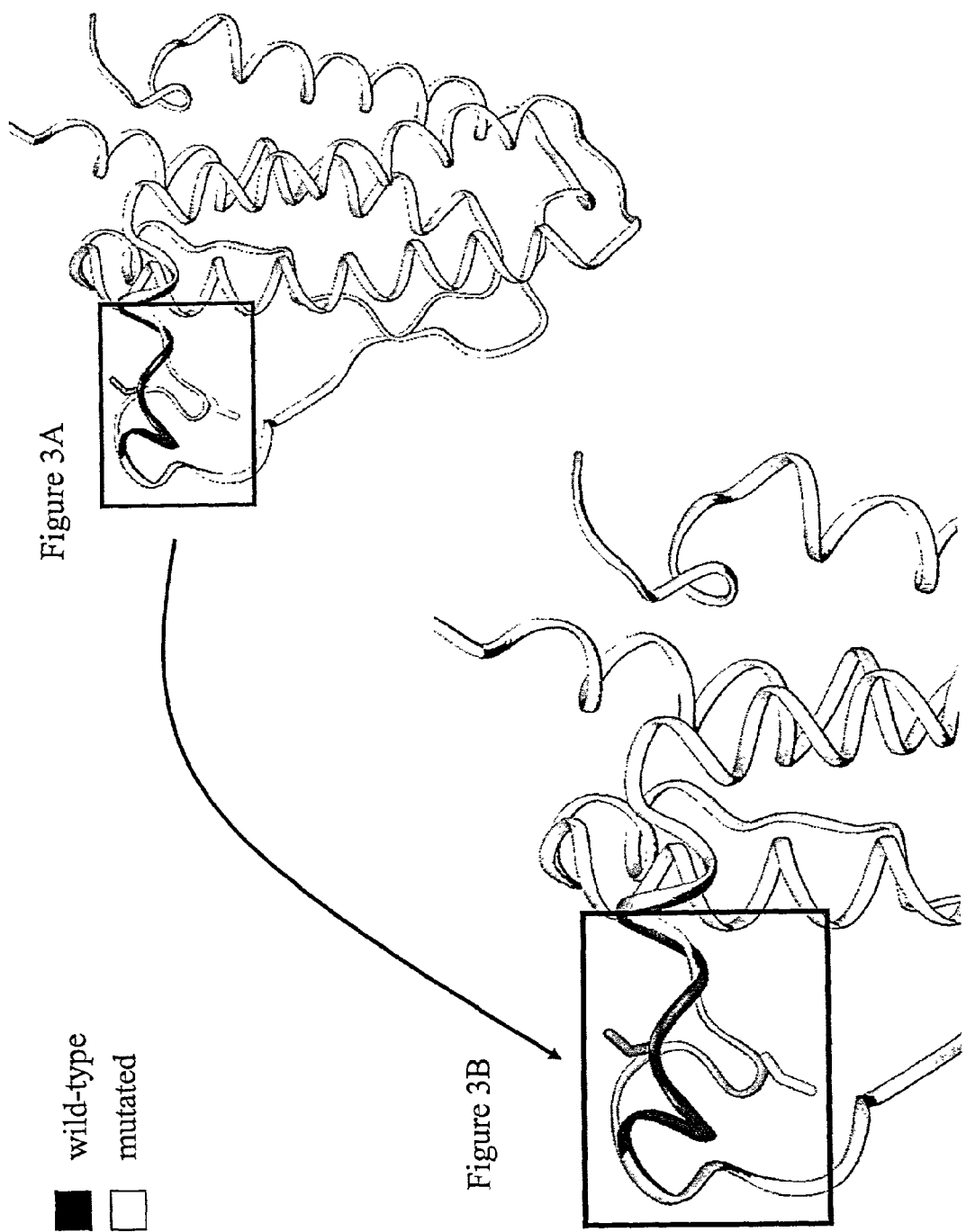

Figure 4A: Experiment n°1
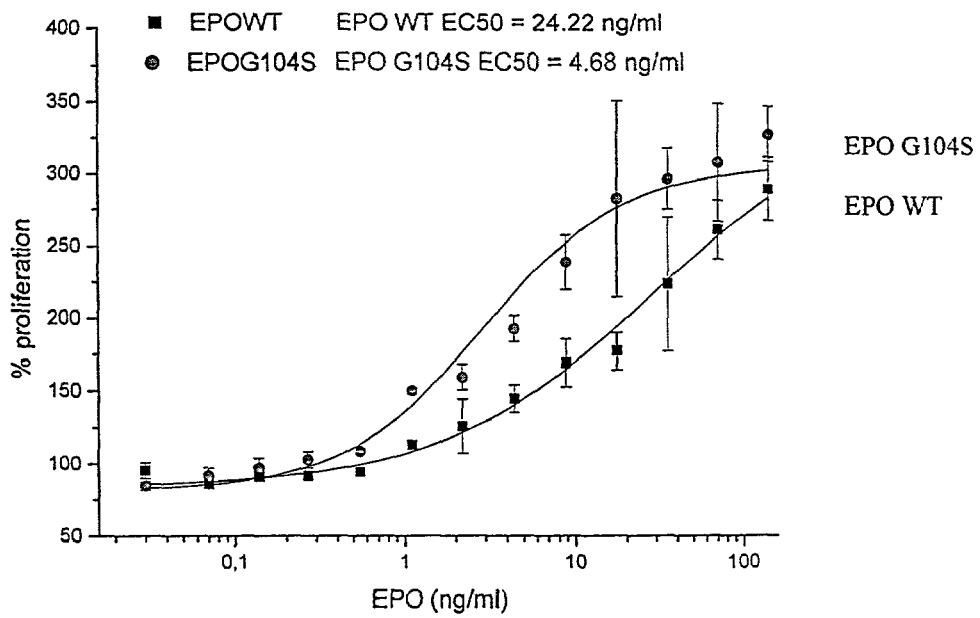
Figure 4B: Experiment n°2
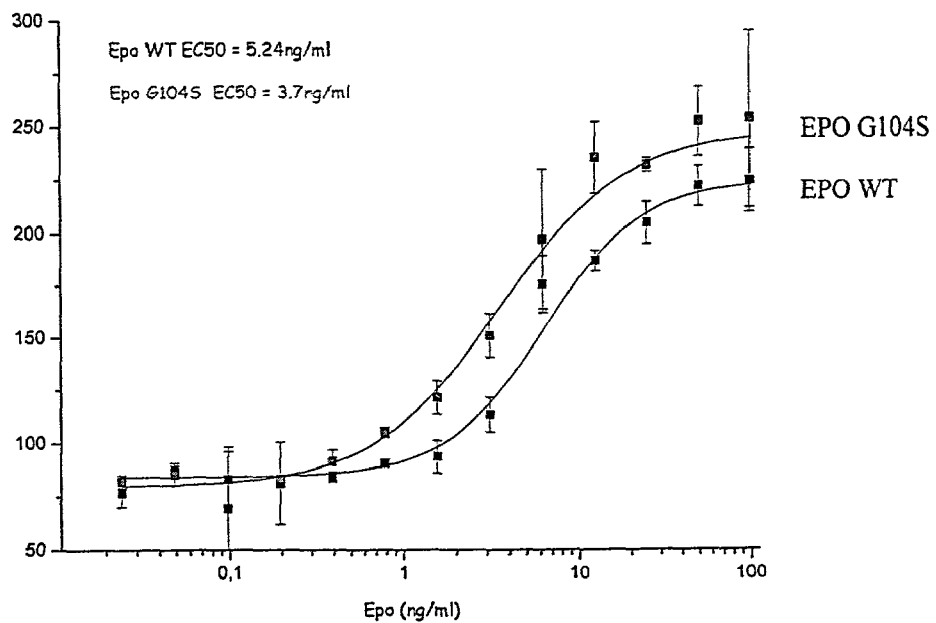

Figure 5
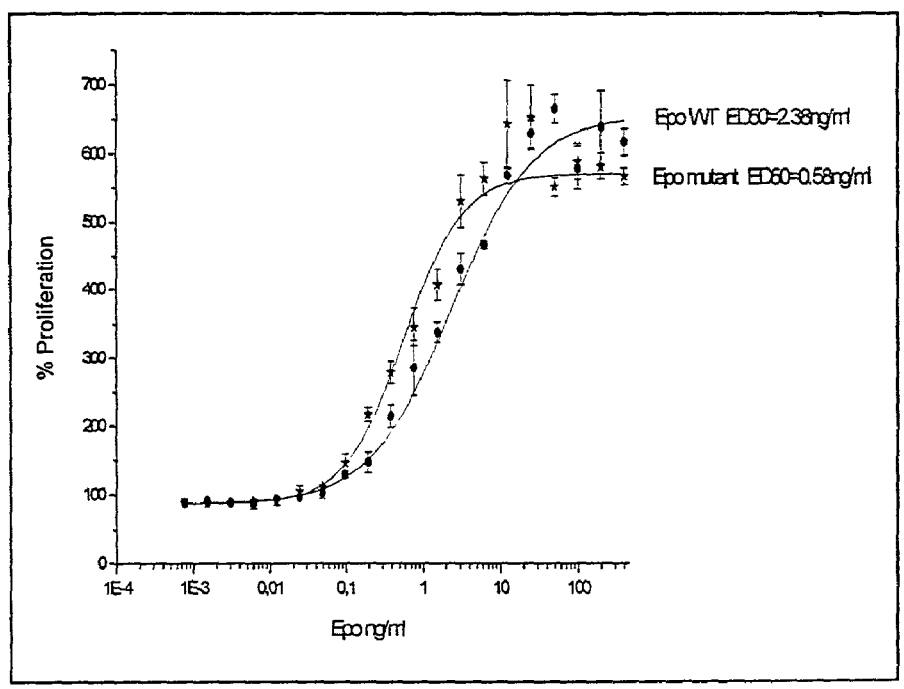
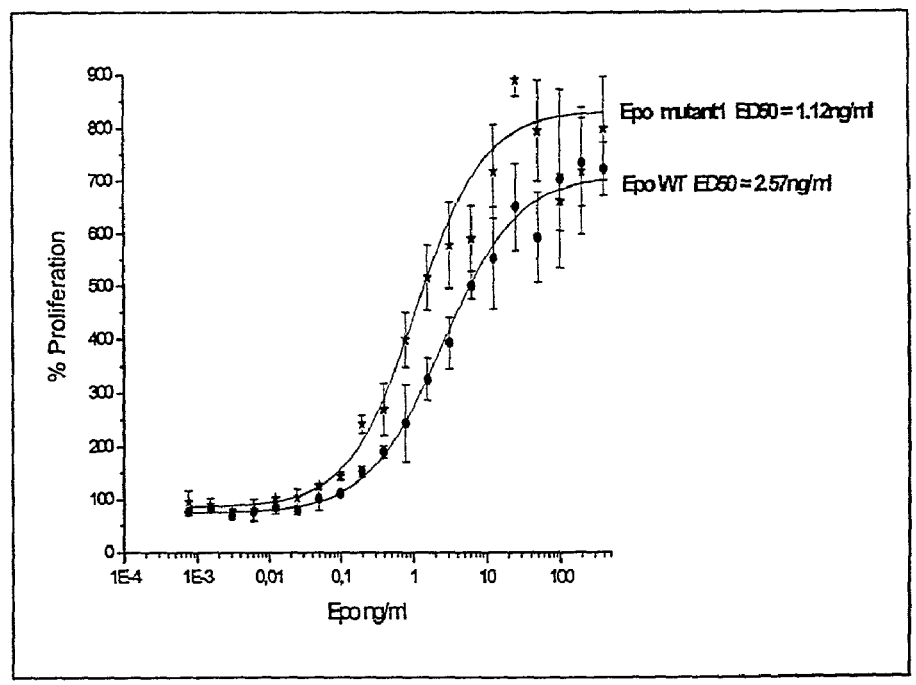

SEQUENCE LISTING

<160> NUMBER OF SEQ ID NOS: 22

<210> SEQ ID NO 1
<211> LENGTH: 3398
<212> TYPE: DNA
<213> ORGANISM: Homo sapiens

<400> SEQUENCE: 1

| | | | | | |
|---|---|---|---|---|---|
| agcttctggg | cttccagacc | cagctacttt | gcggaactca | gcaacccagg | catctctgag | 60 |
| tctccgccca | agaccgggat | gcccccagg | aggtgtccgg | gagcccagcc | tttcccagat | 120 |
| agcagctccg | ccagtcccaa | gggtgcgcaa | ccggctgcac | tcccctcccg | cgacccaggg | 180 |
| cccgggagca | gccccatga | cccacacgca | cgtctgcagc | agcccgtca | gccccggagc | 240 |
| ctcaacccag | gcgtcctgcc | cctgctctga | ccccgggtgg | cccctacccc | tggcgacccc | 300 |
| tcacgcacac | agcctctccc | ccaccccac | ccgcgcacgc | acacatgcag | ataacagccc | 360 |
| cgaccccgg | ccagagccgc | agagtccctg | gccaccccg | gccgctcgct | gcgctgcgcc | 420 |
| gcaccgcgct | gtcctcccgg | agccggaccg | gggccaccgc | gcccgctctg | ctccgacacc | 480 |
| gcgcccctg | gacagccgcc | ctctcctcca | ggcccgtggg | gctggccctg | caccgccgag | 540 |
| cttcccggga | tgagggcccc | cggtgtggtc | accggcgcc | ccaggtcgct | gagggacccc | 600 |
| ggccaggcgc | ggagatgggg | gtgcacggtg | agtactcgcg | ggctgggcgc | tcccgcccgc | 660 |
| ccgggtccct | gtttgagcgg | ggatttagcg | ccccggctat | tggccaggag | gtggctgggt | 720 |
| tcaaggaccg | gcgacttgtc | aaggaccccg | gaaggggag | ggggtgggg | cagcctccac | 780 |
| gtgccagcgg | ggacttgggg | gagtccttgg | ggatggcaaa | aacctgacct | gtgaagggga | 840 |
| cacagtttgg | gggttgaggg | gaagaaggtt | tggggggttc | tgctgtgcca | gtggagagga | 900 |
| agctgataag | ctgataaccct | gggcgctgga | gccaccactt | atctgccaga | ggggaagcct | 960 |
| ctgtcacacc | aggattgaag | tttggccgga | gaagtggatg | ctggtagcct | ggggtgggg | 1020 |
| tgtgcacacg | gcagcaggat | tgaatgaagg | ccagggaggc | agcacctgag | tgcttgcatg | 1080 |
| gttgggaca | ggaaggacga | gctggggcag | agacgtgggg | atgaaggaag | ctgtccttcc | 1140 |
| acagccaccc | ttctccctcc | ccgcctgact | ctcagcctgg | ctatctgttc | tagaatgtcc | 1200 |
| tgcctggctg | tggcttctcc | tgtccctgct | gtcgctccct | ctgggcctcc | cagtcctggg | 1260 |
| cgccccacca | cgcctcatct | gtgacagccg | agtcctgcag | aggtacctct | ggaggccaa | 1320 |
| ggaggccgag | aatatcacgg | tgagacccct | tccccagcac | attccacaga | actcacgctc | 1380 |
| agggcttcag | ggaactcctc | ccagatccag | gaacctggca | cttggtttgg | ggtggagttg | 1440 |
| ggaagctaga | cactgccccc | ctacataaga | ataagtctgg | tggccccaaa | ccatacctgg | 1500 |
| aaactaggca | aggagcaaag | ccagcagatc | ctacgcctgt | ggccagggcc | agagccttca | 1560 |
| gggacccttg | actccccggg | ctgtgtgcat | ttcagacggg | ctgtgctgaa | cactgcagct | 1620 |
| tgaatgagaa | tatcactgtc | ccagacacca | agttaatttt | ctatgcctgg | aagaggatgg | 1680 |
| aggtgagttc | ctttttttttt | tttttccctt | tcttttggag | aatctcattt | gcgagcctga | 1740 |
| ttttggatga | aagggagaat | gatcgaggga | aaggtaaaat | ggagcagcag | agatgaggct | 1800 |
| gcctgggcgc | agaggctcac | gtctataatc | ccaggctgag | atggccgaga | tgggagaatt | 1860 |
| gcttgagccc | tggagtttca | gaccaaccta | ggcagcatag | tgagatcccc | catctctaca | 1920 |
| aacatttaaa | aaaattagtc | aggtgaagtg | gtgcatggtg | gtagtcccag | atatttggaa | 1980 |
| ggctgaggcg | ggaggatcgc | ttgagcccag | gaatttgagg | ctgcagtgag | ctgtgatcac | 2040 |

-continued

```
accactgcac tccagcctca gtgacagagt gaggccctgt ctcaaaaaag aaaagaaaaa    2100
agaaaaataa tgagggctgt atggaatacg ttcattattc attcactcac tcactcactc    2160
attcattcat tcattcattc aacaagtctt attgcatacc ttctgtttgc tcagcttggt    2220
gcttggggct gctgaggggc aggagggaga gggtgacatc cctcagctga ctcccagagt    2280
ccactccctg taggtcgggc agcaggccgt agaagtctgg cagggcctgg ccctgctgtc    2340
ggaagctgtc ctgcggggcc aggccctgtt ggtcaactct tcccagccgt gggagcccct    2400
gcagctgcat gtggataaag ccgtcagtgg ccttcgcagc ctcaccactc tgcttcgggc    2460
tctgggagcc caggtgagta ggagcggaca cttctgcttg ccctttctgt aagaagggga    2520
gaagggtctt gctaaggagt acaggaactg tccgtattcc ttccctttct gtggcactgc    2580
agcgacctct tgttttctcc ttggcagaag gaagccatct cccctccaga tgcggcctca    2640
gctgctccac tccgaacaat cactgctgac actttccgca aactcttccg agtctactcc    2700
aatttcctcc ggggaaagct gaagctgtac acagggagg cctgcaggac agggacaga    2760 tgaccaggtg tgtccacctg gcatatccac ccacctccct caccaacatt gcttgtgcca    2820
caccctcccc cgccactcct gaaccccgtc gaggggctct cagctcagcg ccagcctgtc    2880
ccatggacac tccagtgcca ccaatgacat ctcagggcc agaggaactg tccagagagc    2940
aactctgaga tctaaggatg tcacagggcc aacttgaggg cccagagcag gaagcattca    3000
gagagcagct ttaaactcag ggacagaccc atgctgggaa gacgcctgag ctcactcggc    3060
accctgcaaa attgatgcca ggacacgctt tggaggcgat ttacctgttt tcgcacctac    3120
catcagggac aggatgacct ggagaactta ggtggcaagc tgtgacttct ccaggtctca    3180
cgggcatggg cactcccttg gtggcaagag ccccttgac accggggtgg tgggaaccat    3240
gaagacagga tgggggctgg cctctggctc tcatgggtc caacttttgt gtattcttca    3300
acctcattga caagaactga aaccaccaat atgactcttg ctttctgtg tttctgggaa    3360 cctccaaatc ccctggctct gtcccactcc tggcagca                            3398
```

<210> SEQ ID NO 2
<211> LENGTH: 193
<212> TYPE: PRT
<213> ORGANISM: Homo sapiens

<400> SEQUENCE: 2

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125
```

```
Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

```
<210> SEQ ID NO 3
<211> LENGTH: 20
<212> TYPE: DNA
<213> ORGANISM: Homo sapiens

<400> SEQUENCE: 3
ttgcataccT tctgtttgct                                            20

<210> SEQ ID NO 4
<211> LENGTH: 19
<212> TYPE: DNA
<213> ORGANISM: Homo sapiens

<400> SEQUENCE: 4
cacaagcaat gttggtgag                                             19

<210> SEQ ID NO 5
<211> LENGTH: 18
<212> TYPE: DNA
<213> ORGANISM: Homo sapiens

<400> SEQUENCE: 5
ttcagggacc cttgactc                                              18

<210> SEQ ID NO 6
<211> LENGTH: 20
<212> TYPE: DNA
<213> ORGANISM: Homo sapiens

<400> SEQUENCE: 6
gatcattctc cctttcatcc                                            20

<210> SEQ ID NO 7
<211> LENGTH: 20
<212> TYPE: DNA
<213> ORGANISM: Homo sapiens

<400> SEQUENCE: 7
ttgcataccT tctgtttgct                                            20

<210> SEQ ID NO 8
<211> LENGTH: 19
<212> TYPE: DNA
<213> ORGANISM: Homo sapiens

<400> SEQUENCE: 8
cacaagcaat gttggtgag                                             19

<210> SEQ ID NO 9
<211> LENGTH: 30
<212> TYPE: DNA
<213> ORGANISM: Homo sapiens
```

```
<400> SEQUENCE: 9
tgcagcttga atgagaatat cactgtccca                                     30

<210> SEQ ID NO 10
<211> LENGTH: 32
<212> TYPE: DNA
<213> ORGANISM: Homo sapiens

<400> SEQUENCE: 10
cctcttccag gcatagaaat taactttggt gt                                  32

<210> SEQ ID NO 11
<211> LENGTH: 20
<212> TYPE: DNA
<213> ORGANISM: Homo sapiens

<400> SEQUENCE: 11
ttggcagaag gaagccatct                                                20

<210> SEQ ID NO 12
<211> LENGTH: 20
<212> TYPE: DNA
<213> ORGANISM: Homo sapiens

<400> SEQUENCE: 12
ctgaggccgc atctggaggg                                                20

<210> SEQ ID NO 13
<211> LENGTH: 22
<212> TYPE: DNA
<213> ORGANISM: Homo sapiens

<400> SEQUENCE: 13
ccagaaggaa gccatctccc ct                                             22

<210> SEQ ID NO 14
<211> LENGTH: 20
<212> TYPE: DNA
<213> ORGANISM: Homo sapiens

<400> SEQUENCE: 14
gctcccagag cccgaagcag                                                20

<210> SEQ ID NO 15
<211> LENGTH: 22
<212> TYPE: DNA
<213> ORGANISM: Homo sapiens

<400> SEQUENCE: 15
cggagccaag ccctgttggt ca                                             22

<210> SEQ ID NO 16
<211> LENGTH: 20
<212> TYPE: DNA
<213> ORGANISM: Homo sapiens

<400> SEQUENCE: 16
caggacagct tccgacagca                                                20

<210> SEQ ID NO 17
<211> LENGTH: 20
<212> TYPE: DNA
<213> ORGANISM: Homo sapiens
```

```
<400> SEQUENCE: 17 atggggtgc acgaatgtcc                                        20

<210> SEQ ID NO 18
<211> LENGTH: 20
<212> TYPE: DNA
<213> ORGANISM: Homo sapiens

<400> SEQUENCE: 18
tcatctgtcc cctgtcctgc                                       20

<210> SEQ ID NO 19
<211> LENGTH: 20
<212> TYPE: DNA
<213> ORGANISM: Homo sapiens

<400> SEQUENCE: 19
atggaccacc tcgggcgtc                                        20

<210> SEQ ID NO 20
<211> LENGTH: 23
<212> TYPE: DNA
<213> ORGANISM: Homo sapiens

<400> SEQUENCE: 20
agagcaagcc acatagctgg ggg                                   23

<210> SEQ ID NO 21
<211> LENGTH: 18
<212> TYPE: DNA
<213> ORGANISM: Homo sapiens

<400> SEQUENCE: 21
gcgcccccgc ctaacctc                                         18

<210> SEQ ID NO 22
<211> LENGTH: 18
<212> TYPE: DNA
<213> ORGANISM: Homo sapiens

<400> SEQUENCE: 22
gcgcccccgc ctaacctc                                         18
```

POLYNUCLEOTIDES AND POLYPEPTIDES OF THE ERYTHROPOIETIN GENE

RELATED APPLICATIONS

Portions of the present application claim priority to French Application No. FR 0104603, filed Apr. 4, 2001, titled <<Nouveaux polynucléotides comportant des polymorphismes de type SNP fonctionnels dans la séquence nucléotidique du géne érythropoïétine (EPO) ainsi que de nouveaux polypeptides codés par ces polynucléotides et leurs utilisations thérapeutiques>>; U.S. Provisional Patent Application No. 60/343163, filed Dec. 21, 2001, titled Erythropoietin Related Molecules and Single Nucleotide Polymorphisms; U.S. Provisional Patent Application No. 60/345,440, filed Jan. 4, 2002, titled Modified Erythropoietin Related Molecules and Single Nucleotide Polymorphisms; and U.S. Provisional Patent Application No. 60/358,598, filed Feb. 21, 2002, titled New Polynucleotides and Polypeptides of the EPO Gene.

BACKGROUND OF THE INVENTION

1. Field of the Invention

The present invention relates to new polynucleotides deriving from the nucleotide sequence of the erythropoietin gene (EPO) and comprising new SNPs, new polypeptides derived from the natural erythropoietin protein and comprising mutations caused by these SNPs as well as their therapeutic uses.

2. Related Art

The erythropoietin gene, hereinafter referred to as EPO, is described in the publication Jacobs K. et al. (1985) "Isolation and characterization of genomic and cDNA clones of human erythropoietin"; Nature 313 (6005), 806–810.

The nucleotide sequence of this gene is accessible under accession number X02158 in the GenBank database.

The erythropoietin protein is known to act on proliferation, differentiation, and maturation of progenitor cells of erythropoiesis. It determines their differentiation and maturation into erythrocytes.

EPO is also known to act as autocrine factor on certain erythroleukemic cells and to be a mitogen and a chemoattractant for endothelial cells.

EPO is also known to stimulate activated and differentiated B-cells and to enhance B-cell immunoglobulin production and proliferation.

EPO synthesis is subject to a complex control circuit which links kidney and bone marrow in a feedback loop. Synthesis depends on venous oxygen partial pressure and is increased under hypoxic conditions.

EPO production is influenced also by a variety of other humoral factors, such as testosterone, thyroid hormone, growth hormone, and catecholamines. In contrast, several cytokines such as IL-1, IL-6, and TNF-alpha, reduce EPO synthesis.

In the cell, binding of EPO to its receptor induces:
a release of membrane phospholipids,
the synthesis of diacyl glycerol,
an increase in intracellular calcium levels,
an increase in intracellular pH, and
an increase in intracellular phospholipase A2 and phospholipase C, the latter inducing fos and myc oncogenes.

Excess of EPO is known to lead to erythrocytosis. This is accompanied by an increase in blood viscosity and cardiac output and may lead also to heart failure and pulmonary hypertension. A significant reduction of platelets is also observed.

Thrombosis is another adverse effect of an excess of EPO.

Pulmonary and cerebral embolism, i.e. the sudden obliteration of a blood vessel by a clot or an extraneous compound transported by the blood, also constitutes a serious adverse effect related to EPO consumption.

However, when the amount of synthesized EPO is too low as it is in the case of severe kidney insufficiencies, anemias are often observed. Thus, EPO is often administered to patients with severe kidney insufficiency, with hematocrit below 0.3, in particular in dialysis patients.

The most important complication in the treatment with EPO is hypertony, the increases in urea, potassium, and phosphate levels, an increase in blood viscosity, an expansion of thrombopoietic progenitor cells and circulating platelets.

EPO is also used to activate erythropoiesis, allowing the collection of autologous donor blood.

Moreover, EPO use has been suggested also for non-renal forms of anemia induced, for example, by chronic infections, inflammatory processes, radiation therapy, and cytostatic drug treatment.

To a certain extent EPO is also a stimulating factor of megakaryocytopoiesis. The activity of EPO is synergized by IL-4.

EPO seems to possess neuroprotective capabilities since it has been demonstrated that EPO protects neurons against cell death induced by ischemia, probably by reducing free radicals production and by reducing oxidative stress effects.

It is known that the EPO gene is involved in different human disorders and/or diseases, such as different cancers like carcinomas, melanomas, myelomas, tumors, leukemia, and cancers of the liver, neck, head, and kidneys; cardiovascular diseases such as brain injury; metabolic diseases such as those not related to the immune system like obesity; infectious diseases, in particular viral infections such as Hepatitis B, Hepatitis C, and AIDS; pneumonia; ulcerative colitis; central nervous system diseases such as Alzheimer's disease, schizophrenia, and depression; tissue or organ graft rejection; wounds healing; anemia; allergy; asthma; multiple sclerosis; osteoporosis; psoriasis; rheumatoid arthritis; Crohn's disease; autoimmune diseases and disorders; genital or venereal warts; gastrointestinal disorders; and disorders related to treatments by chemotherapy.

The inventors have found new polypeptide and new polynucleotide analogs to the EPO gene capable of having a different functionality from the natural wild-type EPO protein.

These new polypeptides and polynucleotides can notably be used to treat or prevent the disorders or diseases previously mentioned and avoid all or part of the disadvantages, which are tied to them.

BRIEF SUMMARY OF THE INVENTION

The invention has as its first object new polynucleotides that differ from the nucleotide sequence of the reference wild-type EPO gene, in that they comprise one or several SNPs (Single Nucleotide Polymorphism).

The nucleotide sequence SEQ ID NO. 1 of the human reference wild-type EPO gene is composed of 3398 nucleotides and comprises a coding sequence of 2149 nucleotides, from nucleotide 615 (start codon) to the nucleotide 2763 (stop codon).

The EPO gene is composed of five exons whose positions on the nucleotide sequence SEQ ID NO. 1 are the following:

Exon 1: from nucleotide 397 to nucleotide 627 (comprises the start codon at position 615).

Exon 2: from nucleotide 1194 to nucleotide 1339.

Exon 3: from nucleotide 1596 to nucleotide 1682.

Exon 4: from nucleotide 2294 to nucleotide 2473.

Exon 5: from nucleotide 2608 to nucleotide 3327 (comprises the stop codon at position 2763).

The applicant has identified 12 SNPs in the nucleotide sequence of the reference wild-type EPO gene.

These 12 SNPs are the following: 465–486 (deletion), c577t, g602c, c1288t, c1347t, t1607c, g1644a, g2228a, g2357a, c2502t, c2621g, g2634a.

It is understood, in the sense of the present invention, that the numbering corresponding to the positioning of the SNP previously defined is relative to the numbering of the nucleotide sequence SEQ ID NO. 1.

The letters a, t, c, and g correspond respectively to the nitrogenous bases adenine, thymine, cytosine and guanine.

The first letter corresponds to the wild-type nucleotide, whereas the last letter corresponds to the mutated nucleotide.

Thus, for example, the SNP g1644a corresponds to a mutation of the nucleotide g (guanine) at position 1644 of the nucleotide sequence SEQ ID NO. 1 of the reference wild-type EPO gene into a nucleotide a (adenine). The SNP 465–486 (deletion) corresponds to a mutation in which the 22 nucleotides from positions 465 to 486 of the nucleotide sequence SEQ ID NO. 1 of the reference wild-type EPO gene have been deleted.

These SNPs have each been identified by the applicant using the determination process described in applicant's patent application FR 00 22894, entitled "Process for the determination of one or several functional polymorphism(s) in the nucleotide sequence of a preselected functional candidate gene and its applications" and filed Dec. 6, 2000, cited here by way of reference.

The process described in this patent application permits the identification of one (or several) preexisting SNP(s) in at least one individual from a random population of individuals.

In the scope of the present invention, a fragment of the nucleotide sequence of the EPO gene, comprising, for example, the coding sequence, was isolated from different individuals in a population of individuals chosen in a random manner.

Sequencing of these fragments was then carried out on certain of these samples having a heteroduplex profile (that is a profile different from that of the reference wild-type EPO gene sequence) after analysis by DHPLC ("Denaturing-High Performance Liquid Chromatography").

The fragment sequenced in this way was then compared to the nucleotide sequence of the fragment of the reference wild-type EPO gene and the SNPs in conformity with the invention identified.

Thus, the SNPs are natural and each of them is present in certain individuals of the world population.

The reference wild-type EPO gene codes for an immature protein of 193 amino acids, corresponding to the amino acid sequence SEQ ID NO. 2, that will be converted to a mature protein of 166 amino acids, by cleavage of the signal peptide that includes the first 27 amino acids.

The structure of the natural wild-type EPO protein comprises four helices called A, B, C, and D. The crystal structure of EPO complexed with the EPO receptor indicates that only the three helices A, C, and D are involved in EPO binding with its receptor (Syed et al. (1998). Efficiency of signaling through cytokine receptors depends critically on receptor orientation. Nature 395:511–516). In addition, site directed mutagenesis studying the active site of EPO demonstrates that changes in amino acids situated in helix B have a limited effect on EPO activity (Eliott et al. (1997). Mapping of the active site of recombinant human erythropoietin. Blood. 89: 493–502; Wen et al. (1994). Erythropoietin structure-function relationships. Identification of functionally important domains. J. Biol. Chem. 269:22839–22846).

Each of the coding SNPs of the invention, namely: g1644a, g2357a, c2621g, causes modifications, at the level of the amino acid sequence, of the protein encoded by the nucleotide sequence of the EPO gene.

These modifications in the amino acid sequence are the following:

The coding SNP g1644a causes a mutation of the amino acid aspartic acid (D) at position 70 in the immature protein of the EPO gene, corresponding to the amino acid sequence SEQ ID NO. 2, in asparagine (N) and at position 43 of the mature protein. In the description of the present invention, one will call the mutation encoded by this SNP D43N or D70N according to whether one refers to the mature protein or to the immature protein respectively.

The coding SNP g2357a causes a mutation of the amino acid glycine (G) at position 104 in the immature protein of the EPO gene, corresponding to the amino acid sequence SEQ ID NO. 2, in serine (S) and at position 77 of the mature protein. In the description of the present invention, one will call the mutation encoded by this SNP G77S or G104S according to whether one refers to the mature protein or to the immature protein respectively.

The coding SNP c2621g causes a mutation of the amino acid serine (S) at position 147 in the immature protein of the EPO gene, corresponding to the amino acid sequence SEQ ID NO. 2, in cysteine (C) and at position 120 of the mature protein. In the description of the present invention, one will call the mutation encoded by this SNP S120C or S147C according to whether one refers to the mature protein or to the immature protein respectively.

The coding SNPs g1644a, g2357a, and c2621g, cause modifications of the spatial conformation of the polypeptides in conformity with the invention compared to the polypeptide encoded by the nucleotide sequence of the wild-type reference EPO gene.

These modifications can be observed by computational molecular modeling, according to methods that are well known to a person skilled in the art, making use of, for example, the modeling tools de novo (for example, SEQ-FOLD/MSI), homology (for example, MODELER/MSI), minimization of the force field (for example, DISCOVER, DELPHI/MSI) and/or molecular dynamics (for example, CFF/MSI).

Examples of such models are given hereinafter in the experimental section.

1/ Computational molecular modeling indicates that the mutation D43N on the mutated mature protein involves a structural modification of the loop located between helix A and helix B of the EPO protein, as well as a variation in the structure of the long loop connecting helices C and D of the EPO protein in the area from P129 to I133 amino acids. Those residues are located in front of the mutated amino acid N43. Since this mutation is located near the short helix F48-R53 involved in the binding to the EPO receptor, it may have an effect on the interaction of the EPO protein with its receptor. The D43 residue is highly conserved in all EPO orthologues. It could form salt bridges with positively charged residues (K45, R131), which are also conserved in EPO orthologues.

Thus, the mutated protein possesses a different three-dimensional conformation from the natural wild-type EPO protein encoded by the wild-type EPO gene.

Computational molecular modeling also predicts that the presence of the asparagine amino acid at position 43 involves a significant modification of the structure and of the function of the natural wild-type EPO protein.

2/ Computational molecular modeling indicates that the mutation G77S on the mature mutated protein involves the total unfolding of the C-terminal end of helix B caused by a steric hindrance with the phenylalanine residue at position 183 on helix D and by an unfavorable interaction between an hydrophilic (serine at position 77) and an hydrophobic (leucine at position 35) amino acids on the loop between helix A and helix B. The G77 residue is buried in the wild-type protein structure.

Thus, the mutated protein possesses a different three-dimensional conformation from the natural wild-type EPO protein encoded by the wild-type EPO gene.

Computational molecular modeling also predicts that the presence of the amino acid serine at position 77 involves a significant modification of the structure and of the function of the natural wild-type EPO protein, notably by altering the affinity of the EPO for its receptor.

3/ Computational molecular modeling indicates that the mutation S120C on the mature mutated protein involves a structural modification located on the loop between helix C and helix D, in particular between the lysine at position 116 and the alanine at position 125. The hydrogen bond between S120 and K116 residues in the wild-type EPO protein structure is disrupted in the mutated protein structure.

Thus, the mutated protein possesses a different three-dimensional conformation from the natural wild-type EPO protein encoded by the wild-type EPO gene.

Computational molecular modeling also predicts that the presence of the cysteine amino acid at position 120 involves a significant modification of the structure and of the function of the natural wild-type EPO protein.

Other SNPs in conformity with the invention, namely: 465–486 (deletion), c577t, g602c, c1288t, c1347t, t1607c, g2228a, c2502t, g2634a, do not involve modification of the protein encoded by the nucleotide sequence of the EPO gene at the level of the amino acid sequence SEQ ID NO. 2.

The SNPs c1288t, t1607c, g2634a are silent and the SNPs 465–486 (deletion), c577t, g602c, c1347t, g2228a, c2502t are non-coding.

Genotyping of the polynucleotides in conformity with the invention can be carried out in such a fashion as to determine the allelic frequency of these polynucleotides in a population. Two examples of genotyping are given, hereinafter in the experimental part, for the SNPs g1644a and c2621g.

The determination of the functionality of the polypeptides of the invention can equally be carried out by a test of their biological activity according to protocols described in the following publications:

Bittorf et al.; "Rapid activation of the MAP kinase pathway in hematopoietic cells by erythropoietin, granulocyte-macrophage colony-stimulating factor and interleukin-3"; Cell Signal; 1994; Mar; 6(3):305–11.

Chretien et al.; "Erythropoietin-induced erythroid differentiation of the human erythroleukemia cell line TF-1 correlates with impaired STAT5 activation"; EMBO J.; Aug. 15, 1996; 15(16):4174–81.

Porteu et al.; "Functional regions of the mouse thrombopoietin receptor cytoplasmic domain: evidence for a critical region which is involved in differentiation and can be complemented by erythropoietin"; Mol. Cell. Biol.; 1996 May; 16(5):2473–82.

Pallard et al.; "Thrombopoietin activates a STAT5-like factor in hematopoietic cells"; EMBO J.; Jun 15, 1995; 14(12):2847–56.

The invention also has for an object the use of polynucleotides and of polypeptides in conformity with the invention as well as of therapeutic molecules obtained and/or identified starting from these polynucleotides and polypeptides, notably for the prevention and the treatment of certain human disorders and/or diseases.

Such molecules are particularly useful to prevent or to treat anemia, in particular in patients under dialysis in renal insufficiency, as well as anemia resulting from chronic infections, inflammatory processes, radiotherapies, chemotherapies, as well as to prevent brain injury.

Such molecules are even more particularly useful to increase the production of autologous blood, notably in patients participating in a differed autologous blood collection program to avoid the use of blood from an other person.

BRIEF DESCRIPTION OF THE DRAWINGS

FIG. 1A represents the modeling of the encoded protein according to the invention comprising the SNP D70N and the natural wild-type erythropoietin.

FIG. 1B represents the modeling of the right part of the mutated and wild-type proteins.

In FIGS. 1A and 1B, the black ribbon represents the structure of the natural wild-type erythropoietin and the white ribbon represents the structure of the mutated erythropoietin (D70N).

FIG. 2A represents the modeling of the encoded protein according to the invention comprising the SNP G104S and the natural wild-type erythropoietin.

FIG. 2B represents the modeling of the inferior part of the mutated and wild-type proteins.

In FIGS. 2A and 2B the black ribbon represents the structure of the natural wild-type erythropoietin and the white ribbon represents the structure of the mutated erythropoietin (G104S).

FIG. 3A represents the modeling of the encoded protein according to the invention comprising the SNP S147C and the natural wild-type erythropoietin.

FIG. 3B represents the modeling of the upper left part of the mutated and wild-type proteins.

In FIGS. 3A and 3B the black ribbon represents the structure of the natural wild-type erythropoietin and the white ribbon represents the structure of the mutated erythropoietin (S147C).

FIG. 4 represents the effect of G104S mutated erythropoietin and wild-type erythropoietin (contained in protein extracts) on proliferation of cells from 32 D murine cell line stably transfected with human erythropoietin receptor.

FIGS. 4A and 4B represent the results from two independent experiments, respectively.

FIG. 5 represents the effect of purified G104S mutated erythropoietin and purified wild-type erythropoietin on proliferation of cells from 32 D murine cell line stably transfected with human erythropoietin receptor.

FIGS. 5A and 5B represent the results from two independent experiments, respectively.

DETAILED DESCRIPTION OF THE INVENTION

Figure 6:
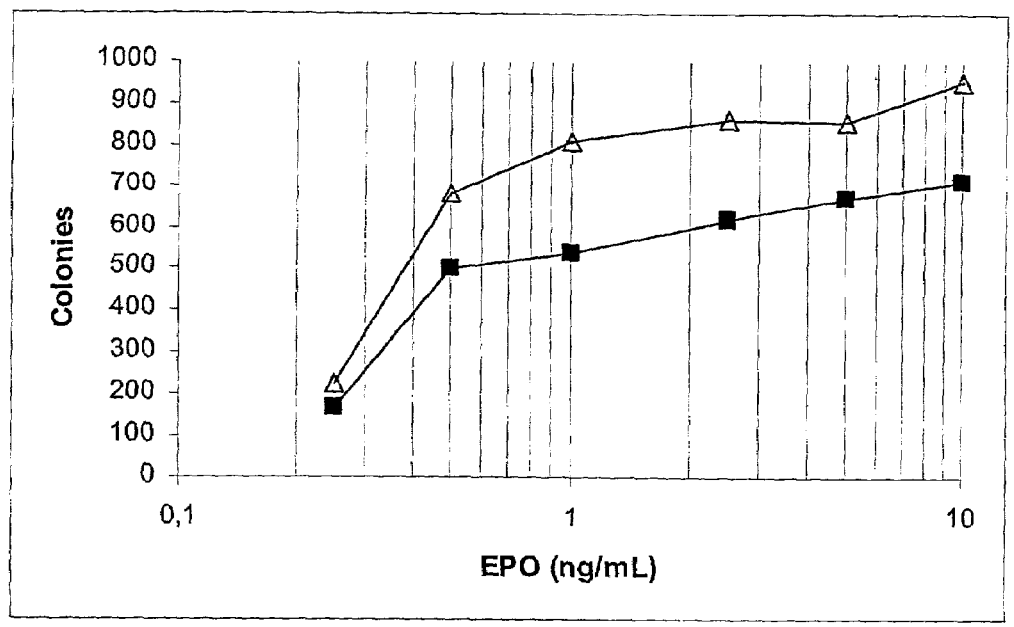
FIG. 6 represents the erythroid colony formation after stimulation by G104S mutated erythropoietin (white triangles) or wild-type erythropoietin (black squares).

Definitions.

"Nucleotide sequence of the reference wild-type gene" is understood as the nucleotide sequence SEQ ID NO. 1 of the human EPO gene which is accessible in GenBank under Accession number X02158 and described in Jacobs K. et al.; "Isolation and characterization of genomic and cDNA clones of human erythropoietin"; Nature 313 (6005), 806–810 (1985).

"Natural wild-type erythropoietin protein" is understood as the mature protein encoded by the nucleotide sequence of the reference wild-type EPO gene. The natural wild-type immature EPO protein corresponds to the peptide sequence SEQ ID NO. 2.

"Polynucleotide" is understood as a polyribonucleotide or a polydeoxyribonucleotide that can be a modified or non-modified DNA or an RNA.

The term polynucleotide includes, for example, a single strand or double strand DNA, a DNA composed of a mixture of one or several single strand region(s) and of one or several double strand region(s), a single strand or double strand RNA and an RNA composed of a mixture of one or several single strand region(s) and of one or several double strand region(s). The term polynucleotide can also include an RNA and/or a DNA including one or several triple strand regions. Polynucleotide is equally understood as the DNAs and RNAs containing one or several bases modified in such a fashion as to have a skeleton modified for reasons of stability or for other reasons. By modified base is understood, for example, the unusual bases such as inosine.

"Polypeptide" is understood as a peptide, an oligopeptide, an oligomer or a protein comprising at least two amino acids joined to each other by a normal or modified peptide bond, such as in the cases of the isosteric peptides, for example.

A polypeptide can be composed of amino acids other than the 20 amino acids defined by the genetic code. A polypeptide can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends.

A polypeptide can be branched following an ubiquitination or be cyclic with or without branching. This type of modification can be the result of natural or synthetic post-translational processes that are well known to a person skilled in the art.

For example, polypeptide modifications is understood to include acetylation, acylation, ADP-ribosylation, amidation, covalent fixation of flavine, covalent fixation of heme, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, cysteine formation, pyroglutamate formation, formylation, gamma-carboxylation, glycosylation including pegylation, GPI anchor formation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature: PROTEINS-STRUCTURE AND MOLECULAR PROPERTIES, $2^{nd}$ Ed., T. E. Creighton, New York, 1993, POST-TRANSLATIONAL COVALENT MODIFICATION OF PROTEINS, B. C. Johnson, Ed., Academic Press, New York, 1983, Seifter et al. "Analysis for protein modifications and nonprotein cofactors", Meth. Enzymol. (1990) 182:626–646 et Rattan et al. "Protein Synthesis: Post-translational Modifications and Aging", Ann NY Acad Sci (1992) 663:48–62.

A "hyperglycosylated polypeptide" or "hyperglycosylated analog of a polypeptide" is understood as a polypeptide whose amino acid sequence has been altered in such a way as to possess at least one more additional glycosylation site or a polypeptide with the same amino acid sequence but whose glycosylation level has been increased.

"Isolated polynucleotide" or "isolated polypeptide" is understood as a polynucleotide or a polypeptide such as previously defined which is isolated from the human body or otherwise produced by a technical process.

"Identity" is understood as the measurement of nucleotide or polypeptide sequences identity. Identity is a term well known to a person skilled in the art and well described in the literature. See COMPUTATIONAL MOLECULAR BIOLOGY, Lesk, A. M., Ed., Oxford University Press, New York, 1998; BIOCOMPUTING INFORMATICS AND GENOME PROJECT, Smith, D. W., Ed., Academic Press, New York, 1993; COMPUTER ANALYSIS OF SEQUENCE DATA, PART I, Griffin, A. M. and Griffin H. G., Ed, Humana Press, New Jersey, 1994; et SEQUENCE ANALYSIS IN MOLECULAR BIOLOGY, von Heinje, G., Academic Press, 1987.

The methods commonly employed to determine the identity and the similarity between two sequences are equally well described in the literature. See GUIDE TO HUGE COMPUTER, Martin J. Bishop, Ed, Academic Press, San Diego, 1994, and Carillo H. and Lipton D., Siam J Applied Math (1988) 48: 1073.

A polynucleotide having, for example, an identity of at least 95% with the nucleotide sequence SEQ ID NO. 1 is a polynucleotide which contains at most 5 points of mutation over 100 nucleotides, compared to said sequence.

These points of mutation can be one (or several) substitution(s), addition(s) and/or deletion(s) of one (or several) nucleotide(s).

In the same way, a polypeptide having, for example, an identity of at least 95% with the amino acid sequence SEQ ID NO. 2 is a polypeptide that contains at most 5 points of mutation over 100 amino acids, compared to said sequence.

These points of mutation can be one (or several) substitution(s), addition(s) and/or deletion(s) of one (or several) amino acid(s).

The polynucleotides and the polypeptides according to the invention which are not totally identical with respectively the nucleotide sequence SEQ ID NO. 1 or the amino acid sequence SEQ ID NO. 2, it being understood that these sequences contains at least one of the SNPs of the invention, are considered as variants of these sequences.

Usually a polynucleotide according to the invention possesses the same or practically the same biological activity as the nucleotide sequence SEQ ID NO. 1 comprising at least one of the SNPs of the invention.

Similarly, usually a polypeptide according to the invention possesses the same or practically the same biological activity as the amino acid sequence SEQ ID NO. 2 comprising at least one of the coding SNPs of the invention.

A variant, according to the invention, can be obtained, for example, by site-directed mutagenesis or by direct synthesis.

"SNP" is understood as any natural variation of a base in a nucleotide sequence. A SNP on a nucleotide sequence can be coding, silent or non-coding.

A coding SNP is a polymorphism included in the coding sequence of a nucleotide sequence that involves a modification of an amino acid in the sequence of amino acids encoded by this nucleotide sequence. In this case, the term SNP applies equally, by extension, to a mutation in an amino acid sequence.

A silent SNP is a polymorphism included in the coding sequence of a nucleotide sequence that does not involve a modification of an amino acid in the amino acid sequence encoded by this nucleotide sequence.

A non-coding SNP is a polymorphism included in the non-coding sequence of a nucleotide sequence. This polymorphism can notably be found in an intron, a splicing zone, a transcription promoter or an enhancer site sequence.

"Functional SNP" is understood as a SNP, such as previously defined, which is included in a nucleotide sequence or an amino acid sequence, having a functionality.

"Functionality" is understood as the biological activity of a polypeptide or of a polynucleotide.

The functionality of a polypeptide or of a polynucleotide according to the invention can consist in a conservation, an augmentation, a reduction or a suppression of the biological activity of the polypeptide encoded by the nucleotide sequence of the wild-type reference gene or of this latter nucleotide sequence.

The functionality of a polypeptide or of a polynucleotide according to the invention can equally consist in a change in the nature of the biological activity of the polypeptide encoded by the nucleotide sequence of the reference wild-type gene or of this latter nucleotide sequence.

The biological activity can, notably, be linked to the affinity or to the absence of affinity of a polypeptide according to the invention with a receptor.

Polynucleotides.

The present invention has for its first object an isolated polynucleotide comprising:
  a) a nucleotide sequence having at least 80% identity, preferably at least 90% identity, more preferably at least 95% identity and still more preferably at least 99% identity with the sequence SEQ ID NO. 1 or its coding sequence (of the nucleotide 615 to the nucleotide 2763), it being understood that this nucleotide sequence comprises at least one of the following coding SNPs: g1644a, g2357a, c2621g, or
  b) a nucleotide sequence complementary to a nucleotide sequence under a).

The present invention relates equally to an isolated polynucleotide comprising:
  a) the nucleotide sequence SEQ ID NO. 1 or its coding sequence, it being understood that each of these sequences comprises at least one of the following coding SNPs: g1644a, g2357a, c2621g, or
  b) a nucleotide sequence complementary to a nucleotide sequence under a).

Preferably, the polynucleotide of the invention consists of the sequence SEQ ID NO. 1 or its coding sequence, it being understood that each of these sequences comprises at least one of the following coding SNPs: g1644a, g2357a, c2621g.

According to the invention, the polynucleotide previously defined comprises a single coding SNP selected from the group consisting of: g1644a, g2357a, and c2621g.

A polynucleotide such as previously defined can equally include at least one of the following non-coding and silent SNPs: 465–486 (deletion), c577t, g602c, c1288t, c1347t, t1607c, g2228a, c2502t, g2634a.

The present invention equally has for its object an isolated polynucleotide comprising or consisting of:
  a) the nucleotide sequence SEQ ID NO. 1 or if necessary its coding sequence, it being understood that each of these sequences comprises at least one of the following non coding or silent SNPs: 465–486 (deletion), c577t, g602c, c1288t, c1347t, t1607c, g2228a, c2502t, g2634a, or
  b) a nucleotide sequence complementary to a nucleotide sequence under a).

It is understood that the following silent SNPs c1288t, t1607c, g2634a, are located in the coding sequence of the nucleotide sequence SEQ ID NO. 1.

The present invention concerns also an isolated polynucleotide consisting of a part of:
  a) a nucleotide sequence SEQ ID NO. 1 or if necessary its coding sequence, it being understood that each of these sequences comprises at least one of the following SNPs: 465–486 (deletion), c577t, g602c, c1288t, c1347t, t1607c, g1644a, g2228a, g2357a, c2502c2621g, g2634a, or
  b) a nucleotide sequence complementary to a nucleotide sequence under a). said isolated polynucleotide being composed of at least 10 nucleotides.

The present invention also has for its object an isolated polynucleotide coding for a polypeptide comprising:
  a) the amino acid sequence SEQ ID NO. 2, or
  b) the amino acid sequence comprising the amino acids included between positions 28 and 193 of the sequence of amino acids SEQ ID NO. 2, it being understood that each of the amino acid sequences under a) and b) comprises at least one of the following coding SNPs: D70N, G104S, S147C.

It is understood, in the sense of the present invention, that the numbering corresponding to the positioning of the D70N, G104S, S147C SNPs is relative to the numbering of the amino acid sequence SEQ ID NO. 2.

According to a preferred object of the invention, the previously defined polypeptide comprises a single coding SNP such as defined above.

More preferably, the present invention also has for its object an isolated polynucleotide coding for a polypeptide comprising all or part of the amino acid sequence SEQ ID NO. 2 and having SNP G104S.

Preferably a polynucleotide according to the invention is composed of a DNA or RNA molecule.

A polynucleotide according to the invention can be obtained by standard DNA or RNA synthetic methods.

A polynucleotide according to the invention can equally be obtained by site-directed mutagenesis starting from the nucleotide sequence of the EPO gene by modifying the wild-type nucleotide by the mutated nucleotide for each SNP on the nucleotide sequence SEQ ID NO. 1.

For example, a polynucleotide according to the invention, comprising a SNP g2357a can be obtained by site-directed mutagenesis starting from the nucleotide sequence of the EPO gene by modifying the nucleotide g by the nucleotide a at position 2357 on the nucleotide sequence SEQ ID NO. 1.

The processes of site-directed mutagenesis that can be implemented in this way are well known to a person skilled in the art. The publication of T A Kunkel in 1985 in "Proc. Natl. Acad. Sci. USA" 82:488 can notably be mentioned.

An isolated polynucleotide can equally include, for example, nucleotide sequences coding for pre-, pro- or pre-pro-protein amino acid sequences or marker amino acid sequences, such as hexa-histidine peptide.

A polynucleotide of the invention can equally be associated with nucleotide sequences coding for other proteins or protein fragments in order to obtain fusion proteins or other purification products.

A polynucleotide according to the invention can equally include nucleotide sequences such as the 5' and/or 3' non-coding sequences, such as, for example, transcribed or non-transcribed sequences, translated or non-translated sequences, splicing signal sequences, polyadenylated sequences, ribosome binding sequences or even sequences which stabilize mRNA.

A nucleotide sequence complementary to the nucleotide or polynucleotide sequence is defined as one that can hybridize with this nucleotide sequence, under stringent conditions.

By "stringent hybridization conditions" is generally but not necessarily understood the chemical conditions that permit a hybridization when the nucleotide sequences have an identity of at least 80%, preferably greater than or equal to 90%, still more preferably greater than or equal to 95% and most preferably greater than or equal to 97%.

The stringent conditions can be obtained according to methods well known to a person skilled in the art and, for example, by an incubation of the polynucleotides, at 42° C., in a solution comprising 50% formamide, 5×SSC (150 mM of NaCl, 15 mM of trisodium citrate), 50 mM of sodium phosphate (pH=7.6), 5× Denhardt Solution, 10% dextran sulfate and 20 µg denatured salmon sperm DNA, followed by washing the filters at 0.1×SSC, at 65° C.

Within the scope of the invention, when the stringent hybridization conditions permit hybridization of the nucleotide sequences having an identity equal to 100%, the nucleotide sequence is considered to be strictly complementary to the nucleotide sequence such as described under a).

It is understood within the meaning of the present invention that the nucleotide sequence complementary to a nucleotide sequence comprises at least one anti-sense SNP according to the invention.

Thus, for example, if the nucleotide sequence comprises the SNP g1644a, its complementary nucleotide sequence comprises the t nucleotide at equivalent of position 1644.

Identification, Hybridization and/or Amplification of a Polynucleotide Comprising a SNP The present invention also has for its object the use of all or part of a previously defined polynucleotide, in order to identify, hybridize and/or amplify all or part of a polynucleotide consisting of the nucleotide sequence SEQ ID NO. 1 or if necessary its coding sequence (of the nucleotide 615 to the nucleotide 2763), it being understood that each one of these sequences comprises at least one of the following SNPs: 465–486 (deletion), c577t, g602c, c1288t, c1347t, t1607c, g1644a, g2228a, g2357a, c2502t, c2621g, g2634a.

Genotyping and Determination of the Frequency of a SNP

The present invention equally has for its object the use of all or part of a polynucleotide according to the invention for the genotyping of a nucleotide sequence which has 90 to 100% identity with the nucleotide sequence of EPO gene and which comprises at least one of the following SNPs: 465–486 (deletion), c577t, g602c, c1288t, c1347t, t1607c, g1644a, g2228a, g2357a, c2502t, c2621g, g2634a.

According to the invention, the genotyping may be carried out on an individual or a population of individuals.

Within the meaning of the invention, genotyping is defined as a process for the determination of the genotype of an individual or of a population of individuals. Genotype consists of the alleles present at one or more specific loci.

"Population of individuals" is understood as a group of determined individuals selected in random or non-random fashion. These individuals can be humans, animals, microorganisms or plants.

Usually, the group of individuals comprises at least 10 persons, preferably from 100 to 300 persons.

The individuals can be selected according to their ethnicity or according to their phenotype, notably those who are affected by the following disorders and/or diseases: cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

The compounds of the invention may preferably be used for the preparation of a therapeutic compound intended to increase the production of autologous blood, notably in patients participating in a differed autologous blood collection program to avoid the use of blood from an other person.

A functional SNP according to the invention is preferably genotyped in a population of individuals.

Many technologies exist which can be implemented in order to genotype SNPs (see notably Kwok Pharmacogenomics, 2000, vol 1, pp 95–100. "High-throughput genotyping assay approaches"). These technologies are based on one of the four following principles: allele specific oligonucleotide hybridization, oligonucleotide elongation by dideoxynucleotides optionally in the presence of deoxynucleotides, ligation of allele specific oligonucleotides or cleavage of allele specific oligonucleotides. Each of these technologies can be coupled to a detection system such as measurement of direct or polarized fluorescence, or mass spectrometry.

Genotyping can notably be carried out by minisequencing with hot ddNTPs (2 different ddNTPs labeled by different fluorophores) and cold ddNTPs (2 different non labeled ddNTPs), in connection with a polarized fluorescence scanner. The minisequencing protocol with reading of polarized fluorescence (FP-TDI Technology or Fluorescence Polarization Template-direct Dye-Terminator Incorporation) is well known to a person skilled in the art.

It can be carried out on a product obtained after amplification by polymerase chain reaction (PCR) of the DNA of each individual. This PCR product is selected to cover the polynucleotide genic region containing the studied SNP. After the last step in the PCR thermocycler, the plate is placed on a polarized fluorescence scanner for a reading of the labeled bases by using fluorophore specific excitation and emission filters. The intensity values of the labeled bases are reported on a graph.

For the PCR amplification, in the case of a SNP of the invention, the sense and antisense primers, respectively, can easily be selected by a person skilled in the art according to the position of the SNPs of the invention.

For example, the sense and antisense nucleotide sequences for the PCR amplification of a fragment whose sequence comprises the SNPs g2228a, g2357a, c2502t, c2621g and/or g2634a can be, respectively:

SEQ ID NO. 3: Sense primer (A): TTGCATACCTTCT-GTTTGCT

SEQ ID NO. 4: Antisense primer (B): CACAAGCAAT-GTTGGTGAG

These nucleotide sequences permit amplification of a fragment having a length of 626 nucleotides, of the nucleotide 2192 to the nucleotide 2817 in the nucleotide sequence SEQ ID NO. 1.

A statistical analysis of the frequency of each allele (allelic frequency) encoded by the gene comprising the SNP in the population of individuals is then achieved, which permits determination of the importance of their impact and their distribution in the different sub-groups and notably, if necessary, the diverse ethnic groups that constitute this population of individuals.

The genotyping data are analyzed in order to estimate the distribution frequency of the different alleles observed in the studied populations. The calculations of the allelic frequencies can be carried out with the help of software such as SAS-suite® (SAS) or SPLUS® (MathSoft). The comparison of the allelic distributions of a SNP of the invention across different ethnic groups of the population of individuals can be carried out by means of the software ARLEQUIN® and SAS-suite®.

The present invention also concerns the use of a polynucleotide according to the invention for the research of one variation in the EPO nucleotide sequence in one individual.

SNPs of the Invention as Genetic Markers

Whereas SNPs modifying functional sequences of genes (e.g. promoter, splicing sites, coding region) are likely to be directly related to disease susceptibility or resistance, all SNPs (functional or not) may provide valuable markers for the identification of one or several genes involved in these disease states and, consequently, may be indirectly related to these disease states (See Cargill et al. (1999). Nature Genetics 22:231–238; Riley et al. (2000). Pharmacogenomics 1:39–47; Roberts L. (2000). Science 287: 1898–1899).

Thus, the present invention also concerns a databank comprising at least one of the following SNPs: 465–486 (deletion), c577t, g602c, c1288t, c1347t, t1607c, g1644a, g2228a, g2357a, c2502t, c2621g, g2634a, in a polynucleotide of the EPO gene.

It is understood that said SNPs are numbered in accordance with the nucleotide sequence SEQ ID NO. 1.

This databank may be analyzed for determining statistically relevant associations between:

(i) at least one of the following SNPs: 465–486 (deletion), c577t, g602c, c1288t, c1347t, t1607c, g1644a, g2228a, g2357a, c2502t, c2621g, g2634a, in a polynucleotide of the EPO gene, and (ii) a disease or a resistance to a disease.

The present invention also concerns the use of at least one of the following SNPs: 465–486 (deletion), c577t, g602c, c1288t, c1347t, t1607c, g1644a, g2228a, g2357a, c2502t, c2621g, g2634a, in a polynucleotide of the EPO gene, for developing diagnostic/prognostic kits for a disease or a resistance to a disease.

A SNP of the invention such as defined above may be directly or indirectly associated to a disease or a resistance to a disease.

Preferably, these diseases may be those which are defined as mentioned above.

Expression Vector and Host Cell

The present invention also has for its object a recombinant vector comprising at least one polynucleotide according to the invention.

Numerous expression systems can be used like, for example, chromosomes, episomes, derived viruses. More particularly, the recombinant vectors used can be derived from bacterial plasmids, transposons, yeast episome, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., $2^{nd}$ Ed., Cold Spring Harbor Laboratory Press, Cold Spring Harbor, N.Y. (1989).

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment.

The present invention also has for its object a host cell comprising a recombinant vector according to the invention.

The introduction of the recombinant vector in a host cell can be carried out according to methods that are well known to a person skilled in the art such as those described in BASIC METHODS IN MOLECULAR BIOLOGY, Davis et al., 1986 and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as cells of streptococci, staphylococci, *E. coli* or *Bacillus subtilis,* cells of fungi such as yeast cells and cells of *Aspergillus, Streptomyces,* insect cells such as cells of *Drosophilia* S2 and of *Spodoptera* Sf9, animal cells, such as CHO, COS, HeLa, C127, BHK, HEK 293 cells and human cells of the subject to treat or even plant cells.

The host cells can be used, for example, to express a polypeptide of the invention or as active product in pharmaceutical compositions, as will be seen hereinafter.

Polypeptides.

The present invention also has for its object an isolated polypeptide comprising an amino acid sequence having at least 80% identity, preferably at least 90% identity, more preferably at least 95% identity and still more preferably at least 99% identity with:
  a) the amino acid sequence SEQ ID NO. 2 or with
  b) the amino acid sequence comprising the amino acids included between positions 28 and 193 of the amino acid sequence SEQ ID NO. 2, it being understood that each of the amino acid sequences under a) and b) contains at least one of the following coding SNPs: D70N, G104S, S147C.

The polypeptide of the invention can equally comprise:
  a) the amino acid sequence SEQ ID NO. 2, or
  b) the amino acid sequence containing the amino acids included between positions 28 and 193 of the amino acid sequence SEQ ID NO. 2, it being understood that each of the amino acid sequences under a) and b) contains at least one of the following coding SNPs: D70N, G104S, S147C.

The polypeptide of the invention can more particularly consist of:
  a) the amino acid sequence SEQ ID NO. 2, or
  b) the amino acid sequence containing the amino acids included between positions 28 and 193 of the amino acid sequence SEQ ID NO. 2, it being understood that each of the amino acid sequences under a) and b) contains at least one of the following coding SNPs: D70N, G104S, S147C.

Preferably, a polypeptide according to the invention contains a single coding SNP selected from the group consisting of: D70N, G104S, and S147C.

More preferably, a polypeptide according to the invention comprises amino acids 28 through 193 of the amino acid sequence SEQ ID NO. 2 and has SNP G104S.

The present invention also concerns a hyperglycosylated analog of a polypeptide according to the invention in order to improve its therapeutic properties.

Preferably, the present invention concerns hyperglycosylated analogs of a polypeptide comprising amino acids 28 through 193 of the amino acid sequence SEQ ID NO. 2 and having SNP G104S.

More preferably, the present invention concerns pegylated analogs of a polypeptide comprising amino acids 28 through 193 of the amino acid sequence SEQ ID NO. 2, and having SNP G104S.

Indeed, it is known in the art that the oligosaccharide component can significantly affect properties relevant to efficacy of a therapeutic glycoprotein, including physical stability, resistance to protease attack, interactions with the immune system, pharmacokinetics and specific biological activity (See, for example, Dube et al. J. Biol. Chem. 263, 17516 (1988); Delorme et al. Biochemistry 31, 9871–9876 (1992)). Whereas human wild-type urinary derived EPO and recombinant wild-type human EPO contain three N-linked and one O-linked oligosaccharide chains, which together comprise about 40% of the total molecular weight of the glycoprotein, it is still possible to increase the number of carbohydrate chains on the protein. Techniques that permit the increase in the number of carbohydrate chains on a protein are well known by the one skilled in the art, including the following:

introduction of new sites available for glycosylation using site-directed mutagenesis creating amino acid residue substitution or addition (see EP0640619 and U.S. patent application Ser. No. 09/853731, published as Publication No. 20020037841, for example).

glycosylation engineering of proteins by using a host cell which harbor the nucleic acid encoding the protein of interest and at least one nucleic acid encoding a glycoprotein-modifying glycosyl transferase as suggested by WO9954342 application.

The present invention equally has for its object a process for the preparation of the above-described polypeptide, in which a previously defined host cell is cultivated in a culture medium and said polypeptide is isolated from the culture medium.

The polypeptide can be purified from the host cells' culture medium, according to methods well known to a person skilled in the art such as precipitation with chaotropic agents such as salts, in particular ammonium sulfate, ethanol, acetone or trichloroacetic acid; acid extraction; ion exchange chromatography; phosphocellulose chromatography; hydrophobic interaction chromatography; affinity chromatography; hydroxyapatite chromatography or exclusion chromatographies.

"Culture medium" is understood as the medium in which the polypeptide of the invention is isolated or purified. This medium can be composed of the extracellular medium and/or the cellular lysate. Techniques well known to a person skilled in the art equally permit him or her to give back an active conformation to the polypeptide, if the conformation of said polypeptide was altered during the isolation or the purification.

Antibodies.

The present invention also has for its object a process for obtaining an immunospecific antibody.

"Antibody" is understood as including monoclonal, polyclonal, chimeric, simple chain, humanized antibodies as well as the Fab fragments, including Fab or immunoglobulin expression library products.

An immunospecific antibody can be obtained by immunization of an animal with a polypeptide according to the invention.

The invention also relates to an immunospecific antibody for a polypeptide according to the invention, such as defined previously.

A polypeptide according to the invention, one of its fragments, an analog, one of its variants or a cell expressing this polypeptide can also be used to produce immunospecific antibodies.

The term "immunospecific" means that the antibody possesses a better affinity for the polypeptide of the invention than for other polypeptides known in the prior art.

The immunospecific antibodies can be obtained by administration of a polypeptide of the invention, of one of its fragments, of an analog or of an epitopic fragment or of a cell expressing this polynucleotide in a mammal, preferably non human, according to methods well known to a person skilled in the art.

For the preparation of monoclonal antibodies, typical methods for antibody production can be used, starting from cell lines, such as the hybridoma technique (Kohler et al., Nature (1975) 256: 495–497), the trioma technique, the human B cell hybridoma technique (Kozbor et al., Immunology Today (1983) 4: 72) and the EBV hybridoma technique (Cole et al., MONOCLONAL ANTIBODIES AND CANCER THERAPY, pp. 77–96, Alan R. Liss, 1985).

The techniques of single chain antibody production such as described, for example, in U.S. Pat. No. 4,946,778 can equally be used.

Transgenic animals such as mice, for example, can equally be used to produce humanized antibodies.

Agents Interacting with the Polypeptide of the Invention

The present invention equally has for its object a process for the identification of an agent activating or inhibiting a polypeptide according to the invention, comprising:

a) the preparation of a recombinant vector comprising a polynucleotide according to the invention containing at least one coding SNP, b) the preparation of host cells comprising a recombinant vector according to a), c) the contacting of host cells according to b) with an agent to be tested, and d) the determination of the activating or inhibiting effect generated by the agent to test.

A polypeptide according to the invention can also be employed for a process for screening compounds that interact with it.

These compounds can be activating (agonists) or inhibiting (antagonists) agents of intrinsic activity of a polypeptide according to the invention. These compounds can equally be ligands or substrates of a polypeptide of the invention. See Coligan et al., Current Protocols in Immunology 1 (2), Chapter 5 (1991).

In general, in order to implement such a process, it is first desirable to produce appropriate host cells that express a polypeptide according to the invention. Such cells can be, for example, cells of mammals, yeasts, insects such as *Drosophilia* or bacteria such as *E. coli*.

These cells or membrane extracts of these cells are then placed in the presence of compounds to be tested.

The binding capacity of the compounds to be tested with the polypeptide of the invention can then be observed, as well as the inhibition or the activation of the functional response.

Step d) of the above process can be implemented by using an agent to be tested that is directly or indirectly labeled. It can also include a competition test, by using a labeled or non-labeled agent and a labeled competitor agent.

It can equally be determined if an agent to be tested generates an activation or inhibition signal on cells expressing the polypeptide of the invention by using detection means appropriately chosen according to the signal to be detected.

Such activating or inhibiting agents can be polynucleotides, and in certain cases oligonucleotides or polypeptides, such as proteins or antibodies, for example.

The present invention also has for its object a process for the identification of an agent activated or inhibited by a polypeptide according to the invention, comprising:

a) the preparation of a recombinant vector comprising a polynucleotide according to the invention containing at least one coding SNP, b) the preparation of host cells comprising a recombinant vector according to a), c) placing the host cells according to b) in the presence of an agent to be tested, and d) the determination of the activating or inhibiting effect generated by the polypeptide on the agent to be tested.

An agent activated or inhibited by the polypeptide of the invention is an agent that responds, respectively, by an activation or an inhibition in the presence of this polypeptide. The agents, activated or inhibited directly or indirectly by the polypeptide of the invention, can consist of polypeptides such as, for example, membranal or nuclear receptors, kinases and more preferably tyrosine kinases, transcription factor or polynucleotides.

Detection of Diseases

The present invention also has for object a process for analyzing the biological characteristics of a polynucleotide according to the invention and/or of a polypeptide according to the invention in a subject, comprising at least one of the following:

a) Determining the presence or the absence of a polynucleotide according to the invention in the genome of a subject;

b) Determining the level of expression of a polynucleotide according to the invention in a subject;

c) Determining the presence or the absence of a polypeptide according to the invention in a subject;

d) Determining the concentration of a polypeptide according to the invention in a subject; and/or e) Determining the functionality of a polypeptide according to the invention in a subject.

These biological characteristics may be analyzed in a subject or in a sample from a subject.

These biological characteristics may permit genetic diagnosis and/or determination of whether a subject is affected or at risk of being affected or, to the contrary, presents a partial resistance to the development of a disease, an indisposition or a disorder linked to the presence of a polynucleotide according to the invention and/or a polypeptide according to the invention. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

This process also permits genetic diagnosis of a disease or resistance to a disease linked to the presence, in a subject, of the mutant allele encoded by a SNP according to the invention.

Preferably, in step a), the presence or absence of a polynucleotide, containing at least one coding SNP such as previously defined, is going to be detected.

The detection of the polynucleotide may be carried out starting from biological samples from the subject to be studied, such as cells, blood, urine, saliva, or starting from a biopsy or an autopsy of the subject to be studied. The genomic DNA may be used for the detection directly or after a PCR amplification, for example. RNA or cDNA can equally be used in a similar fashion.

It is then possible to compare the nucleotide sequence of a polynucleotide according to the invention with the nucleotide sequence detected in the genome of the subject.

The comparison of the nucleotide sequences can be carried out by sequencing, by DNA hybridization methods, by mobility difference of the DNA fragments on an electrophoresis gel with or without denaturing agents or by melting temperature difference. See Myers et al., Science (1985) 230: 1242. Such modifications in the structure of the nucleotide sequence at a precise point can equally be revealed by nuclease protection tests, such as RNase and the S1 nuclease or also by chemical cleaving agents. See Cotton et al., Proc. Nat. Acad. Sci. USA (1985) 85: 4397–4401. Oligonucleotide probes comprising a polynucleotide fragment of the invention can equally be used to conduct the screening.

Many methods well known to a person skilled in the art can be used to determine the expression of a polynucleotide of the invention and to identify the genetic variability of this polynucleotide (See Chee et al., Science (1996), Vol 274, pp 610–613).

In step b), the level of expression of the polynucleotide may be measured by quantifying the level of RNA encoded by this polynucleotide (and coding for a polypeptide) according to methods well known to a person skilled in the art as, for example, by PCR, RT-PCR, RNase protection, Northern blot, and other hybridization methods.

In step c) and d) the presence or the absence as well as the concentration of a polypeptide according to the invention in a subject or a sample from a subject may be carried out by well known methods such as, for example, by radioimmunoassay, competitive binding tests, Western blot and ELISA tests.

Consecutively to step d), the determined concentration of the polypeptide according to the invention can be compared with the natural wild-type EPO protein concentration usually found in a subject.

A person skilled in the art can identify the threshold above or below which appears the sensitivity or, to the contrary, the resistance to the disease, the indisposition or the disorder evoked above, with the help of prior art publications or by conventional tests or assays, such as those that are previously mentioned.

In step e), the determination of the functionality of a polypeptide according to the invention may be carried out by methods well known to a person skilled in the art as, for example, by in vitro tests such as above mentioned or by an use of host cells expressing said polypeptide.

Therapeutic Compounds and Treatments of Diseases

The present invention also has for its object a therapeutic compound containing, by way of active agent, a polypeptide according to the invention and/or a hyperglycosylated analog of the polypeptide comprising amino acids 28 through 193 of the amino acid sequence SEQ ID NO. 2 and having SNP G104S.

The invention also relates to the use of a polypeptide according to the invention and/or a hyperglycosylated analog of the polypeptide comprising amino acids 28 through 193 of the amino acid sequence SEQ ID NO. 2 and having SNP G104S, for the manufacture of a therapeutic compound intended for the prevention or the treatment of different human disorders and/or diseases. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

The compounds of the invention may preferably be used for the preparation of a therapeutic compound intended to increase the production of autologous blood, notably in patients participating in a differed autologous blood collection program to avoid the use of blood from an other person.

Preferably, a polypeptide according to the invention and/or a hyperglycosylated analog of the polypeptide comprising amino acids 28 through 193 of the amino acid sequence SEQ ID NO. 2 and having SNP G104S can also be used for the manufacture of a therapeutic compound intended:

to prevent or treat anemia, in particular in patients under dialysis in renal insufficiency, as well as anemia resulting from chronic infections, inflammatory processes, radiotherapies, chemotherapies, and/or to increase the production of autologous blood, notably in patients participating in a differed autologous blood collection program to avoid the use of blood from an other person, and/or to prevent brain injury.

Certain of the compounds permitting to obtain the polypeptide according to the invention as well as the compounds obtained or identified by or from this polypeptide can likewise be used for the therapeutic treatment of the human body, i.e. as a therapeutic compound.

This is why the present invention also has for an object a therapeutic compound containing, by way of active agent, a polynucleotide according to the invention containing at least one previously defined SNP, a previously defined recombinant vector, a previously defined host cell, and/or a previously defined antibody.

The invention also relates to the use of a polynucleotide according to the invention containing at least one previously defined SNP, a previously defined recombinant vector, a previously defined host cell, and/or a previously defied antibody for the manufacture of a therapeutic compound intended for the prevention or the treatment of different human disorders and/or diseases such as cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

The compounds of the invention may preferably be used for the preparation of a therapeutic compound intended to increase the production of autologous blood, notably in patients participating in a differed autologous blood collection program to avoid the use of blood from an other person.

Preferably, the invention concerns the use of a polynucleotide according to the invention containing at least one previously defined SNP, a previously defined recombinant vector, a previously defined host cell, and/or a previously defined antibody for the manufacture of a therapeutic compound intended:

to prevent or treat anemia, in particular in patients under dialysis in renal insufficiency, as well as anemia resulting from chronic infections, inflammatory processes, radiotherapies, chemotherapies, and/or to increase the production of autologous blood, notably in patients participating in a differed autologous blood collection program to avoid the use of blood from an other person, and/or to prevent brain injury.

The dosage of a polypeptide and of the other compounds of the invention, useful as active agent, depends on the choice of the compound, the therapeutic indication, the mode of administration, the nature of the formulation, the nature of the subject and the judgment of the doctor.

When it is used as active agent, a polypeptide according to the invention is generally administered at doses ranging between 1 and 300 units/kg of the subject.

The invention also has as an object a pharmaceutical composition that contains, as active agent, at least one above-mentioned compound such as a polypeptide according to the invention; a hyperglycosylated analog of the polypeptide comprising amino acids 28 through 193 of the amino acid sequence SEQ ID NO. 2 and having SNP G104S; a polynucleotide according to the invention containing at least one previously defined SNP, a previously defined recombinant vector, a previously defined host cell, and/or a previously defined antibody, as well as a pharmaceutically acceptable excipient.

In these pharmaceutical compositions, the active agent is advantageously present at physiologically effective doses.

These pharmaceutical compositions can be, for example, solids or liquids and be present in pharmaceutical forms currently used in human medicine such as, for example, simple or coated tablets, gelcaps, granules, caramels, suppositories and preferably injectable preparations and powders for injectables. These pharmaceutical forms can be prepared according to usual methods.

The active agent(s) can be incorporated into excipients usually employed in pharmaceutical compositions such as talc, Arabic gum, lactose, starch, dextrose, glycerol, ethanol, magnesium stearate, cocoa butter, aqueous or non-aqueous vehicles, fatty substances of animal or vegetable origin, paraffinic derivatives, glycols, various wetting agents, dispersants or emulsifiers, preservatives.

The active agent(s) according to the invention can be employed alone or in combination with other compounds such as therapeutic compounds such as other cytokines such as interleukine or interferons, for example.

The different formulations of the pharmaceutical compositions are adapted according to the mode of administration.

The pharmaceutical compositions can be administered by different routes of administration known to a person skilled in the art.

The invention equally has for an object a diagnostic composition that contains, as active agent, at least one above-mentioned compound such as a polypeptide according to the invention, all or part of a polynucleotide according to the invention, a previously defined recombinant vector, a previously defined host cell, and/or a previously defined antibody, as well as a suitable pharmaceutically acceptable excipient.

This diagnostic composition may contain, for example, an appropriate excipient like those generally used in the diagnostic composition such as buffers and preservatives.

The present invention equally has as an object the use:

a) of a therapeutically effective quantity of a polypeptide according to the invention, and/or b) of a polynucleotide according to the invention, and/or c) of a host cell from the subject to be treated, previously defined, to prepare a therapeutic compound intended to increase the expression or the activity, in a subject, of a polypeptide according to the invention.

Thus, to treat a subject who needs an increase in the expression or in the activity of a polypeptide of the invention, several methods are possible.

It is possible to administer to the subject a therapeutically effective quantity of a polypeptide of the invention; of a hyperglycosylated analog of the polypeptide comprising amino acids 28 through 193 of the amino acid sequence SEQ ID NO. 2 and having SNP G104S; and/or of the activating agent and/or activated agent such as previously defined, possibly in combination, with a pharmaceutically acceptable excipient.

It is likewise possible to increase the endogenous production of a polypeptide of the invention by administering a polynucleotide according to the invention to the subject. For example, this polynucleotide can be inserted in a retroviral expression vector. Such a vector can be isolated from cells having been infected by a retroviral plasmid vector containing RNA encoding for the polypeptide of the invention, in such a fashion that the transduced cells produce infectious viral particles containing the gene of interest. See Gene Therapy and other Molecular Genetic-based Therapeutic Approaches, Chapter 20, in Human Molecular Genetics, Strachan and Read, BIOS Scientifics Publishers Ltd (1996).

In accordance with the invention, a polynucleotide containing at least one coding SNP such as previously defined is going to be preferably used.

It is equally possible to administer to the subject host cells belonging to him (autologous cells), these host cells having been preliminarily taken and modified so as to express the polypeptide of the invention, as previously described.

The present invention equally relates to the use:

a) of a therapeutically effective quantity of a previously defined immunospecific antibody, and/or b) of a polynucleotide permitting inhibition of the expression of a polynucleotide according to the invention, and/or c) of a host cell from the subject to be treated, as previously defined in order to prepare a therapeutic compound intended to reduce the expression or the activity, in a subject, of a polypeptide according to the invention.

Thus, it is possible to administer to the subject a therapeutically effective quantity of an inhibiting agent and/or of an antibody such as previously defined, possibly in combination, with a pharmaceutically acceptable excipient.

It is equally possible to reduce the endogenous production of a polypeptide of the invention by administration to the subject of a complementary polynucleotide according to the invention permitting inhibition of the expression of a polynucleotide of the invention.

Preferably, a complementary polynucleotide containing at least one coding SNP such as previously defined can be used.

The present invention concerns also the use of a erythropoietin protein and/or hyperglycosylated analog for the preparation of a therapeutic compound for the prevention or the treatment of a patient having a disorder or a disease caused by a EPO variant linked to the presence in the genome of said patient of a nucleotide sequence having at least 95% identity (preferably, 97% identity, more preferably 99% identity and particularly 100% identity) with the nucleotide sequence SEQ ID NO. 1, provided that said nucleotide sequence comprises one of the following SNPs: 465–486 (deletion), c577t, g602c, c1288t, c1347t, t1607c, g1644a, g2228a, g2357a, c2502t, c2621g, g2634a.

Preferably, said therapeutic compound is used for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

The compounds of the invention may preferably be used for the preparation of a therapeutic compound intended to increase the production of autologous blood, notably in patients participating in a differed autologous blood collection program to avoid the use of blood from an other person.

Mimetic Compounds of an EPO Polypeptide Comprising the SNP G104S

The present invention also concerns a new compound having a biological activity substantially similar or higher in comparison to that of the polypeptide of:

a) amino acid sequence SEQ ID NO. 2, or b) amino acid sequence comprising the amino acids included between positions 28 and 193 of the amino acid sequence SEQ ID NO. 2;

provided that said amino acid sequences under a) and b) comprise the G104S SNP.

Said biological activity may be evaluated, for example, by measuring cellular proliferative activity on cells from murine 32D cell line over-expressing the EPO receptor, erythroid colony formation or binding capacity to EPO receptor.

As mentioned in the experimental part, the G104S mutated EPO increases cellular proliferation of murine 32D cell line over-expressing the EPO receptor 2 to 5 times more than the wild-type EPO.

As mentioned in the experimental section, the G104S mutated EPO has a higher capacity to stimulate erythroid colony formation than the wild-type EPO.

As mentioned in the experimental part, the binding capacity of G104S mutated EPO to EPO receptor is higher than that measured with the natural wild-type EPO.

A new compound of the invention, such as previously defined, may possess a biological activity substantially similar to that of the G104S mutated EPO, i.e. which is higher than that of the natural wild-type EPO.

Said compound may also have a biological activity which is even higher than that of the G104S mutated EPO.

A compound according to the invention may have at least one function associated with EPO acting upon an EPO receptor and an activity substantially similar to that of polypeptide of amino acid sequence SEQ ID NO. 2 comprising the G104S SNP.

Said compound may also have at least one function associated with EPO acting upon an EPO receptor based on activity induced by effecting a change at said EPO receptor substantially similar to an effect upon such EPO receptor induced by a polypeptide of amino acid sequence SEQ ID NO. 2 comprising the G104S SNP.

Said compound may be a biochemical compound, such as a polypeptide or a peptide for example, or an organic chemical compound, such as a synthetic peptide-mimetic for example.

The present invention also provides a new compound having a cellular proliferative activity on cells from murine 32D cell line over-expressing the EPO receptor that is 2 to 5 times higher than that of wild-type EPO.

The present invention also provides a new compound having a higher capacity to stimulate erythroid colony formation than wild-type EPO.

The present invention also provides a new compound having a binding capacity to EPO receptor that is higher than that of wild-type EPO.

The present invention also concerns the use of a polypeptide of the invention containing the G104S SNP, for the identification of a compound such as defined above.

The present invention also concerns a process for the identification of a compound of the invention, comprising the following steps:
 a) Determining the biological activity, such as stimulating effect on cell proliferation of 32D cell lines over-expressing the human EPO-receptor, on erythroid colony formation, and/or binding capacity to EPO receptor, for example;
 b) Comparing:
  i) the activity determined in step a) of the compound to be tested, with
  ii) the activity of the polypeptide of amino acid sequence SEQ ID NO. 2, or of amino acid sequence comprising the amino acids included between 28 and 193 of the amino acid sequence SEQ ID NO. 2;
  provided that said amino acid sequences comprise the G104S SNP; and
 c) Determining, on the basis of the comparison carried out in step b), whether the compound to be tested has a substantially similar or higher activity compared to that of the polypeptide of amino acid sequence SEQ ID NO. 2, or of amino acid sequence comprising the amino acids included between positions 28 and 193 of the amino acid sequence SEQ ID NO. 2; provided that said amino acid sequences comprise the G104S SNP.

Preferably, the compound to be tested may be previously identified from synthetic peptide combinatorial libraries, high-throughput screening, or designed by computer-aided drug design so as to have the same three-dimensional structure and/or chemical effect as that of the polypeptide of amino acid sequence SEQ ID NO. 2, or of amino acid sequence comprising the amino acids included between position 28 and 193 of the amino acid sequence SEQ ID NO. 2, provided that said amino acid sequences comprise the G104S SNP.

The methods to identify and design compounds are well known by a person skilled in the art.

Publications referring to these methods may be, for example:

Silverman R. B. (1992). "Organic Chemistry of Drug Design and Drug Action". Academic Press, 1st edition (Jan. 15, 1992).

Anderson S and Chiplin J. (2002). "Structural genomics; shaping the future of drug design? Drug Discov. Today. 7(2):105–107.

Selick H E, Beresford A P, Tarbit M H. (2002). "The emerging importance of predictive ADME simulation in drug discovery". Drug Discov. Today. 7(2):109–116.

Burbidge R, Trotter M, Buxton B, Holden S. (2001). "Drug design by machine learning: support vector machines for pharmaceutical data analysis". Comput. Chem. 26(1): 5–14.

Kauvar L. M. (1996). "Peptide mimetic drugs:a comment on progress and prospects" 14(6): 709.

The compounds of the invention may be used for the preparation of a therapeutic compound intended for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, gastrointestinal disorders, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said cardiovascular diseases may include brain injury and anemias including anemia in patients under dialysis in renal insufficiency, as well as anemia resulting from chronic infections, inflammatory processes, radiotherapies, and chemotherapies.

Said metabolic diseases may include such non-immune associated diseases as obesity.

Said diseases of the central nervous system may include Alzheimer's disease, Parkinson's disease, schizophrenia and depression.

Said diseases and disorders may also include wound healing and osteoporosis.

The compounds of the invention may preferably be used for the preparation of a therapeutic compound intended to increase the production of autologous blood, notably in patients participating in a differed autologous blood collection program to avoid the use of blood from an other person.

EXPERIMENTAL SECTION

Example 1

Modeling of the Protein Encoded by a Polynucleotide of Nucleotide Sequence Containing the SNP g1644a, g2357a, or c2621g and of the Protein Encoded by the Nucleotide Sequence of the Wild-Type Reference Gene In a first step, the three-dimensional structure of erythropoietin was constructed starting from that available in the PDB database (code 1EER) and by using the software Modeler (MSI, San Diego, Calif.). The mature polypeptide fragment was then modified in such a fashion as to reproduce the mutation D70N, G104S or S147C. A thousand molecular minimization steps were conducted on this mutated fragment by using the programs AMBER and DISCOVER (MSI: Molecular Simulations Inc.). Two molecular dynamic calculation runs were then carried out with the same program and the same force fields. In each case, 50,000 steps were calculated at 300° K., terminated by 300 equilibration steps. The result of this modeling is shown in FIGS. 1, 2, and 3.

Example 2

Genotyping of the SNPs g1644a and c2621g in a Population of Individuals

The genotyping of SNPs is based on the principle of the minisequencing wherein the product is detected by a reading of polarized fluorescence. The technique consists of a fluorescent minisequencing (FP-TDI Technology or Fluorescence Polarization Template-direct Dye-terminator Incorporation). The minisequencing is performed on a product amplified by PCR from genomic DNA of each individual of the population. This PCR product is chosen in such a manner that it covers the genic region containing the SNP to be genotyped. After elimination of the PCR primers and the dNTPs that have not been incorporated, the minisequencing is carried out. The minisequencing consists of lengthening an oligonucleotide primer, placed just upstream of the site of the SNP, by using a polymerase enzyme and fluorolabeled dideoxynucleotides. The product resulting from this lengthening process is directly analyzed by a reading of polarized fluorescence. All these steps, as well as the reading, are carried out in the same PCR plate.

Thus, the genotyping requires 5 steps:
1) Amplification by PCR
2) Purification of the PCR product by enzymatic digestion
3) Elongation of the oligonucleotide primer
4) Reading
5) Interpretation of the reading Step 1) Amplification by PCR.

The PCR amplification of the nucleotide sequence of the EPO gene is carried out starting from genomic DNA coming from 268 individuals of ethnically diverse origins. These genomic DNAs were provided by the Coriell Institute in the United States. The 268 individuals are distributed as follows:

| Phylogenic Population | Specific Ethnic Population | Total | % |
|---|---|---|---|
| African American | African American | 50 | 100.0 |
|  | Subtotal | 50 | 18.7 |
| Amerind | South American Andes | 10 | 66.7 |
|  | South West American Indians | 5 | 33.3 |
|  | Subtotal | 15 | 5.6 |
| Caribbean | Caribbean | 10 | 100.0 |
|  | Subtotal | 10 | 3.7 |
| European Caucasoid | North American Caucasian | 79 | 79.8 |
|  | Iberian | 10 | 10.1 |
|  | Italian | 10 | 10.1 |
|  | Subtotal | 99 | 36.9 |
| Mexican | Mexican | 10 | 100.0 |
|  | Subtotal | 10 | 3.7 |
| Northeast Asian | Chinese | 10 | 50.0 |
|  | Japanese | 10 | 50.0 |
|  | Subtotal | 20 | 7.5 |
| Non-European Caucasoid | Greek | 8 | 21.6 |
|  | Indo-Pakistani | 9 | 24.3 |
|  | Middle-Eastern | 20 | 54.1 |
|  | Subtotal | 37 | 13.8 |
| Southeast Asian | Pacific Islander | 7 | 41.2 |
|  | South Asian | 10 | 58.8 |
|  | Subtotal | 17 | 6.3 |
| South American | South American | 10 | 100.0 |
|  | Subtotal | 10 | 3.7 |
|  | Total | 268 | 100 |

* Phylogenic populations are adapted from:
Cavalli-Sforza, P. Menozzi, and A. Piazza. 1994. "The History and Geography of Human Genes." Princeton: Princeton University Press. pp 80.

The genomic DNA coming from each one of these individuals constitutes a sample.

The PCR amplification is carried out from primers which can easily be designed by the person skilled in the art on the basis of the nucleotide sequence SEQ ID NO. 1.

For the genotyping of g1644a, the PCR amplification is carried out using the following primers:

SEQ ID NO. 5: Sense primer: TTCAGGGACCCT-TGACTC

SEQ ID NO. 6: Antisense primer: GATCATTCTC-CCTTTCATCC

These nucleotide sequences permit amplification of a fragment of a length of 208 nucleotides, from the nucleotide 1557 to the nucleotide 1764 in the nucleotide sequence SEQ ID NO. 1.

For the genotyping of c2621g, the PCR amplification is carried out using the following primers:

SEQ ID NO. 7: Sense primer: TTGCATACCTTCT-GTTTGCT

SEQ ID NO. 8: Antisense primer: CACAAGCAATGT-TGGTGAG

These nucleotide sequences permit amplification of a fragment of a length of 626 nucleotides, from the nucleotide 2192 to the nucleotide 2817 in the nucleotide sequence SEQ ID NO. 1.

For each SNP to be genotyped, the PCR product will serve as a template for the minisequencing.

The total reaction volume of the PCR reaction is 5 μl per sample. This reaction volume is composed of the reagents indicated in the following table:

| Supplier | Reference | Reactant | Initial Conc. | Vol. per tube (μl) | Final Conc. |
|---|---|---|---|---|---|
| Life Technology | Delivered w/Taq | Buffer (X) | 10 | 0.5 | 1 |
| Life Technology | Delivered w/Taq | MgSO$_4$ (mM) | 50 | 0.2 | 2 |
| AP Biotech | 27-2035-03 | dNTPs (mM) | 10 | 0.1 | 0.2 |
| | On request | Sense Primer (μM) | 10 | 0.1 | 0.2 |
| | On request | Antisense Primer (μM) | 10 | 0.1 | 0.2 |
| Life Technology | 11304-029 | Taq platinum | 5U/μl | 0.02 | 0.1 U/rxn |
| | | H$_2$O | Qsp 5 μl | 1.98 | |
| | | DNA (sample) | 2.5 ng/μl | 2 | 5 ng/rxn |
| | | Total volume | | 5 μl | |

These reagents are distributed in a black PCR plate having 384 wells provided by ABGene (ref:TF-0384-k). The plate is sealed, centrifuged, then placed in a thermocycler for 384-well plates (Tetrad of MJ Research) and undergoes the following incubation: PCR Cycles: 1 min at 94° C., followed by 36 cycles composed of 3 steps (15 sec. at 94° C., 30 sec. at 56° C., 1 min at 68° C.).

Step 2) Purification of the PCR product by enzymatic digestion.

The PCR amplified product is then purified using two enzymes: Shrimp Alkaline Phosphatase (SAP) and exonuclease I (Exo I). The first enzyme permits the dephosphorylation of the dNTPs which have not been incorporated during the PCR amplification, whereas the second eliminates the remaining single stranded DNA, in particular the primers which have not been used during the PCR. This digestion is done by addition, in each well of the PCR plate, of a reaction mixture of 5 μl per sample.

This reaction mixture is composed of the following reagents:

| Supplier | Reference | Reactant | Initial Conc | Vol./tube (μl) | Final conc. |
|---|---|---|---|---|---|
| AP Biotech | E70092X | SAP | 1 U/μl | 0.5 | 0.5/rxn |
| AP Biotech | 070073Z | Exo I | 10 U/μl | 0.1 | 1/rxn |
| AP Biotech | Supplied w/SAP | Buffer SAP (X) | 10 | 0.5 | 1 |
| | | H$_2$O | Qsp 5 μl | 3.9 | |
| | | PCR product | | 5 μl | |
| | | Total vol. | | 10 μl | |

Once filled, the plate is sealed, centrifuged, then placed in a thermocycler for 384-well plates (Tetrad of MJ Research) and undergoes the following incubation: Digestion SAP-EXO: 45 min at 37° C., 15 min at 80° C.

Step 3) Elongation of the oligonucleotide primer

The elongation or minisequencing step is then carried out on this digested PCR product by addition of a reaction mixture of 5 μl per prepared sample, as indicated in the following table:

| Supplier | Reference | Reactant | Initial conc. | Vol. per tube (μl) | Final conc. |
|---|---|---|---|---|---|
| Own preparation | | Elongation Buffer[1] (X) | 5 | 1 | 1 |
| Life Technologies | On request | Miniseq Primer (μM) A or B | 10 | 0.5 | 1 |
| AP Biotech | 27-2051 (61, 71, 81)-01 | ddNTPs[2] (μM) 2 are non labeled | 2.5 of each | 0.25 of each | 0.125 of each |
| NEN | Nel 472/5 and Nel 492/5 | ddNTPs[2] (μM) 2 are labeled with Tamra and R110 | 2.5 of each | 0.25 of each | 0.125 of each |
| AP Biotech | E79000Z | Thermo-sequenase | 3.2 U/μl | 0.125 | 0.4 U/reaction |
| | | H$_2$O | Qsp 5 μl | 3.125 | |
| | | digested PCR product | | 10 | |
| | | Total volume | | 15 | |

The sequences of the two minisequencing primers necessary for the genotyping were determined in a way to correspond to the sequence of the nucleotides located upstream of the site of a SNP according to the invention. The PCR product that contains the SNP being a double stranded DNA product, the genotyping can therefore be done either on the sense strand or on the antisense strand. The selected primers are manufactured by Life Technologies Inc.

For the SNP g1644a, the minisequencing primers tested are the following:

SEQ ID NO. 9: Sense primer (A): tgcagcttgaatgagaatatcactgtccca

SEQ ID NO. 10: Antisense primer (B): cctcttccaggcatagaaattaactttggtgt

The minisequencing of the SNP g1644a was first validated over 48 samples, then genotyped over the set of the population of individuals composed of 268 individuals and 11 negative controls. Several minisequencing conditions were tested and the following optimal condition was retained for the genotyping of g1644a:

Antisense primer+ddCTP-R110+ddTTP-Tamra

For the SNP c2621 g, the minisequencing primers tested are the following:

SEQ ID NO. 11: Sense primer (A): ttggcagaaggaagccatct

SEQ ID NO. 12: Antisense primer (B): ctgaggccgcatctggaggg

The minisequencing of the SNP c2621g was first validated over 48 samples, then genotyped over the set of the population of individuals composed of 268 individuals and 10 negative controls. Several minisequencing conditions were tested and the following optimal condition was retained for the genotyping of c2621g:

Sense primer+ddCTP-R110+ddGTP-Tamra

Once filled, the plate is sealed, centrifuged, then placed in a thermocycler for 384-well plates (Tetrad of MJ Research) and undergoes the following incubation: Elongation cycles: 1 min. at 93° C., followed by 35 cycles composed of 2 steps (10 sec. at 93° C., 30 sec. at 55° C.).

After the last step in the thermocycler, the plate is directly placed on a polarized fluorescence reader of type Analyst® HT of LJL Biosystems Inc. The plate is read using Criterion Host® software by using two methods. The first permits reading the Tamra labeled base by using emission and excitation filters specific for this fluorophore (excitation 550-10 nm, emission 580-10 nm) and the second permits reading the R110 labeled base by using the excitation and emission filters specific for this fluorophore (excitation 490-10 nm, emission 520-10 nm). In the two cases, a dichroic double mirror (R110/Tamra) is used and the other reading parameters are:

Z-height: 1.5 mm
Attenuator: out
Integration time: 100,000 μsec.
Raw data units: counts/sec
Switch polarization: by well
Plate settling time: 0 msec
PMT setup: Smart Read (+), sensitivity 2
Dynamic polarizer: emission
Static polarizer: S A file result is thus obtained containing the calculated values of mP (milliPolarization) for the Tamra filter and that for the R110 filter. These mP values are calculated from the intensity values obtained on the parallel plane (//) and on the perpendicular plane (⊥) according to the following formula:

$$mP=1000(//-g\bot)/(//+g\bot).$$

In this calculation, the value ⊥ is weighted by a factor g. It is a machine parameter that must be determined experimentally beforehand.

Steps 4) and 5) Interpretation of the reading and determination of the genotypes.

The mP values are reported on a graph using Microsoft Inc. Excel software, and/or Allele Caller® software developed by LJL Biosystems Inc.

On the abscissa is indicated the mP value of the Tamra labeled base, on the ordinate is indicated the mP value of the R110 labeled base. A strong mP value indicates that the base labeled with this fluorophore is incorporated and, conversely, a weak mP value reveals the absence of incorporation of this base.

Up to three homogenous groups of nucleotide sequences having different genotypes are obtained.

The use of the Allele Caller® software permits, once the identification of the different groups is carried out, to directly extract the genotype defined for each individual in table form.

Results of the Minisequencing for the SNPs g1644a and c2621 g.

After the completion of the genotyping process, the determination of the genotypes of the individuals of the population of individuals for the two functional SNPs studied here was carried out using the graphs described above.

For the SNP g1644a, this genotype is in theory either homozygote GG, or heterozygote GA or homozygote AA in the tested individuals. In reality, and as shown below, the homozygote genotype AA is not detected in the population of individuals.

Similarly, for the SNP c2621g, this genotype is in theory either homozygote CC, or heterozygote CG, or homozygote GG in the tested individuals. In reality, and as shown below, the homozygote genotype GG is not detected in the population of individuals.

The results of the negative controls, of the distribution of the determined genotypes in the population of individuals and the calculation of the different allelic frequencies for these two functional SNPs are presented in the following tables:

| | Number of individuals | | Number of controls | | Percentage of success |
|---|---|---|---|---|---|
| | tested | genotyped | tested | genotyped | |
| g1644a | 268 | 267 | 11 | 11 | 99.6 |
| c2621g | 268 | 250 | 10 | 10 | 93.5 |

| | | | | g1644a (D70N) | | | | | |
|---|---|---|---|---|---|---|---|---|---|
| Phylogenic Population | Total | f | (95% CI) | GG | % | GA | % | AA | % | Total |
| African American | 50 | | | 50 | 100 | | | | | 50 |
| Amerind | 15 | | | 15 | 100 | | | | | 15 |

-continued

| | | | | | | | | | | |
|---|---|---|---|---|---|---|---|---|---|---|
| Caribbean | 10 | | | 10 | 100 | | | | | 10 |
| European Caucasoid | 99 | 0.5 | (0, 1.5) | 97 | 99.0 | 1 | 1.0 | | | 98 |
| Mexican | 10 | | | 10 | 100 | | | | | 10 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | | | 17 | 100 | | | | | 17 |
| Total | 268 | 0.2 | (0, 0.6) | 266 | 99.6 | 1 | 0.4 | | | 267 |

| | | c2621g (S147C) | | | | | | | | |
|---|---|---|---|---|---|---|---|---|---|---|
| Phylogenic Population | Total | f | (95% CI) | CC | % | CG | % | GG | % | Total |
| African American | 50 | | | 50 | 100 | | | | | 50 |
| Amerind | 15 | | | 15 | 100 | | | | | 15 |
| Caribbean | 10 | | | 10 | 100 | | | | | 10 |
| European Caucasoid | 99 | 0.5 | (0, 1.6) | 91 | 98.9 | 1 | 1.1 | | | 92 |
| Mexican | 10 | | | 8 | 100 | | | | | 8 |
| Non-European Caucasoid | 37 | | | 32 | 100 | | | | | 32 |
| Northeast Asian | 20 | | | 19 | 100 | | | | | 19 |
| South American | 10 | | | 8 | 100 | | | | | 8 |
| Southeast Asian | 17 | | | 16 | 100 | | | | | 16 |
| Total | 268 | 0.2 | (0, 0.6) | 249 | 99.6 | 1 | 0.4 | | | 250 |

In the above table.

N represents the number of individuals.

% represents the percentage of individuals in the specific sub-population.

the allelic frequency represents the percentage of the mutated allele in the specific sub-population.

95% IC represents the minimal and maximal interval of confidence at 95%

By examining these results by population, it is observed that, in the case of SNP g1644a, the only heterozygote individual GA comes from the sub-population European Caucasoid of the population of individuals.

Similarly, by examining these results by population, it is observed that, in the case of SNP c2621g, the only heterozygote individual CG comes from the sub-population European Caucasoid of the population of individuals.

Example 3

Study of the Biological Function of G104S Mutated Erythropoietin Compared to that of Natural Wild-Type Erythropoietin The first step consists of preparing mutated and wild-type EPO proteins a) Cloning of the Natural Wild-Type Erythropoietin and Mutated Erythropoietin (g2357a) in the Eukaryotic Expression Vector pcDNA3.1/His-Topo Carrying the Geneticin-Resistance Gene In comparison to the sequence of the erythropoietin protein published in SwissProt, the polyhistidine tagged EPO cDNA from the Genestorm clone (H-X02158M-Invitrogen) harbored the K143E ($G_{427}AG$) mutation (the number in subscript corresponds to the nucleotide position on the cDNA sequence). Thus, we first restituted the natural wild-type E143 ($A_{427}AG$) sequence using the Exsite PCR kit (Stratagene) and the following primers:

SEQ ID NO. 13: Sense primer: CCAGAAGGAAGC-CATCTCCCCT

SEQ ID NO. 14: Antisense primer (phosphorylated on the 5' end): GCTCCCAGAGCCCGAAGCAG In parallel, the G104S ($G_{310}GC$=>AGC) mutated erythropoietin was obtained using the Exsite PCR kit (Stratagene corp.) and the following primers:

SEQ ID NO. 15: Sense primer: CGGAGCCAAGCCCT-GTTGGTCA

SEQ ID NO. 16: Antisense primer (phosphorylated on the 5' end): CAGGACAGCTTCCGACAGCA To remove the polyhistidine tail and isolate the nucleotide sequences corresponding to the complete EPO protein (i.e. natural signal peptide and mature protein), whether mutated or wild-type form, a PCR amplification was carried out using the following primers:

SEQ ID NO. 17: Sense primer: ATGGGGGTGCAC-GAATGTCC

SEQ ID NO. 18: Antisense primer: TCATCTGTCCCCT-GTCCTGC

The PCR products are inserted in the eukaryotic expression vector pcDNA3.1/GS/HisTopo (TOPO™-cloning; Invitrogen Corp.) under the control of the CMV promoter. This vector allows the constitutive expression of proteins in eukaryotic cell lines.

After checking of the nucleotide sequence of the vector region coding for the recombinant proteins, the different recombinant expression vectors are transfected into the Chinese Hamster Ovary cells (CHO) using Superfect (QIAgen).

b) Selection of Clones Over-Expressing Natural Wild-Type or Mutated EPO

Two days after the transfection with the various EPO constructs, the CHO cells are placed in a culture medium containing 800 µg/ml of Geneticin (Invitrogen). As a result of a 2-week growth in these culture conditions, stable cells over-expressing EPO are selected. The cells are then cloned by the limited dilution method. Thirty clones from cells transfected with either wild-type or mutated EPO are screened for expression of the EPO protein using an EPO ELISA (R&D Systems). Several EPO-expressing clones are picked and kept frozen. Among them, the clone producing the highest amount of either wild-type or mutated EPO was used for EPO mass production.

c) Purification of EPO Proteins

After EPO expression in the CHO culture, the culture medium is centrifuged at 1500 rpm for 20 minutes permitting recovery of the supernatant. The supernatant is then concentrated 10 times using Labscale (Millipore membrane 5 Kda), dialyzed against 3 liters of buffer Tris 50 mM, NaCl 25 mM pH 9 and purified on an anion exchange column (Pharmacia, HiprepQ). After protein elution using a step at 200 mM NaCl, the protein is desalted against buffer $NaH_2PO_4$ 50 mM, NaCl 25 mM, pH 7 and purified on Heparine HP (Pharmacia). Protein elution is then carried out using a step at 150 mM NaCl. Finally, the EPO protein is analyzed by SDS-PAGE gel characterization followed by a quantification using densitometry (Biorad densitometer GS800).

The second step consists of preparing 32D murine cells over-expressing the EPO receptor.

d) Cloning of the Natural EPO Receptor in the Eukaryotic Expression Vector pcDNA3.1/GS/HisTopo Carrying the Zeocyn-Resistance Gene:

To further insert the cDNA in frame with the V5 epitope and a polyhistidine tail, the complete sequence of the natural human EPO receptor cDNA from the Genestorm clone (H-M60459M—Invitrogen) is amplified by PCR using the following primers:

SEQ ID NO.19: Sense primer: ATGGACCAC-CTCGGGGCGTC

SEQ ID NO.20: Antisense primer: AGAGCAAGCCA-CATAGCTGGGGG

The PCR product is inserted into the eukaryotic expression vector pcDNA3.1/GS/HisTopo (TOPO™-cloning; Invitrogen Corp.) under the control of the CMV promoter. This vector allows constitutive expression of proteins in eukaryotic cells lines. In this case, the EPO receptor is tagged with an additional C-terminal sequence containing a poly-histidine tail and a V5 epitope. After checking of the nucleotide sequence of the vector region coding for the recombinant receptor, the construct was electroporated into the murine 32D cell line (ATCC)

e) Selection of Stable Cells Over-Expressing the EPO-Receptor.

To select stable cells over-expressing the human EPO-Receptor, the 32D cell line electroporated with the construct encoding the EPO-Receptor was cultivated in the presence of 200 μg/ml of Zeocin (Invitrogen) for 5 weeks before its ability to proliferate in the presence of commercial human EPO (R&D Systems) was assessed.

Finally, the biological effect of mutated EPO and wild-type EPO is determined by two different tests: by evaluation of the ability of the different EPO proteins to induce cell proliferation of murine 32 cells over-expressing the EPO receptor and by measurement of the direct binding of mutated EPO and wild-type EPO to EPO receptor.

f) Evaluation of the Ability of Wild-Type and Mutated G104S EPO to Induce Cell Proliferation of Murine 32D Cells Over-Expressing the EPO-Receptor.

The ability of wild-type EPO and G104S mutated EPO to induce cell proliferation is assessed on murine 32D cells over-expressing the EPO-Receptor (32D-EPOR cells). This test was performed first on protein extracts containing the different EPO proteins produced in the previous steps, and, second, on purified EPO proteins obtained as previously described.

The principle is that 32D-EPOR cells are inoculated in a 96-well plate at a cell density of $2.10^4$ cells/well in a 200 μl final culture medium containing 10% fetal calf serum. 32D-EPOR cells are incubated with serial dilutions of either wild-type or mutated EPO (from 0.024 to 140 ng/ml in the case of protein extracts and from $0.76 \times 10^{-3}$ to 400 ng/ml in the case of purified EPO), at 37° C., for 5 days after which Uptiblue (Uptima) is added to the cultures. The rate of cell proliferation is quantified by measuring the fluorescence emitted at 590 nm (excitation 560 nm) after an additional period of incubation of 24 hours in the case of protein extracts and 4 hours in the case of purified EPO.

The proliferative activity of the natural wild-type and the mutated EPO is based on the determination of the EC50 value corresponding to the EPO concentration (ng/ml) for which cell proliferation reaches 50%.

First, two experiments such as described above have been carried out using the proteins extracts containing EPO, each experiment being repeated three times. The results of these experiments are represented in FIG. 4A and FIG. 4B, respectively. In FIG. 4, for each protein concentration, the points correspond to the average of the three measures and the standard deviation represents the variation between the three repeats.

The EC values obtained from these curves are the following:

in the first experiment: 24.22 ng/ml for the wild-type EPO and 4.68 ng/ml for the G104S mutated EPO in the second experiment: 5.24 ng/ml for the wild-type EPO and 3.7 ng/ml for the G104S mutated EPO Thus, FIGS. 4A and 4B and the EC50 values indicate that the G104S mutated EPO stimulating effect on cell proliferation of 32D cell lines over-expressing the human EPO-Receptor is 2 to 5 times higher than that of the natural wild-type EPO.

Second, similar experiments have been carried out using purified EPO proteins. The results of two experiments, performed in triplicates, are represented in FIG. 5A and FIG. 5B, respectively. In FIG. 5, for each protein concentration, the points correspond to the average of the three measures and the standard deviation represents the variation between the three repeats.

The EC50 values obtained from these curves are the following:

in the first experiment: 2.38 ng/ml for the wild-type EPO and 0.58 ng/ml for the G104S mutated EPO in the second experiment: 2.57 ng/ml for the wild-type EPO and 1.12 ng/ml for the G104S mutated EPO.

Thus, FIGS. 5A and 5B and the EC50 values indicate that the purified G104S mutated EPO stimulating effect on cell proliferation of 32D cell lines over-expressing the human EPO-Receptor is 2 to 5 times higher than that of the purified natural wild-type EPO, confirming the results obtained with the protein extracts.

g) Stimulation of Erythroid Colony Formation by G104S Mutated Erythropoietin

The capacity of G104S mutated erythropoietin to stimulate erythroid colony formation was evaluated and compared to that of wild-type erythropoietin.

To do so, human bone marrow cells from healthy individuals were collected and separated on a ficoll gradient. Nucleated cells ($2.5 \times 10^5$ cells) were plated in semisolid methyl cellulose. Mutated or wild-type erythropoietin ranging from 0.25 to 10 ng/mL was then added to the culture medium. After 10 days of culture, erythroid colonies were counted.

This experiment was performed twice and the average results are collected in the following table and represented in FIG. 6.

|  | Number of colonies | |
| --- | --- | --- |
| EPO (ng/mL) | Wild-type EPO | G104S EPO |
| 0.25 | 170 | 230 |
| 0.5 | 505 | 685 |
| 1 | 540 | 810 |
| 2.5 | 620 | 860 |
| 5 | 670 | 855 |
| 10 | 715 | 950 |

These data clearly demonstrate that G104S mutated erythropoietin stimulates erythroid colony formation. In particular, stimulation of erythroid colony formation by G104S mutated erythropoietin is 30 to 50% higher than that measured with wild-type erythropoietin.

h) Interaction Between EPO and the EPO Receptor

The interaction between EPO and its receptor (EPO-R) was determined using Surface Plasmon Resonance technology (Biacore, SPR).

To compare the affinities of G104S mutated EPO and wild-type EPO, quantitative measurements of the binding interaction between EPO and the extra-cellular part of the EPO-R are carried out using the EPO-R target ligand immobilized on a sensor chip surface and then passing, on the chip, different concentrations of an analyte consisting of the EPO proteins to be tested.

The carboxymethylated dextran layer of the chip is designed to bind nickel to mediate the capture of ligands via metal chelation of a poly-histidine tail.

For this reason, we designed an EPO-Receptor corresponding to the extra-cellular part of the mature human receptor (amino-acids 25–247) followed by a C-terminal V5 epitope and a poly-histidine tail. The corresponding cDNA fragment was inserted into the *Pichia pastoris* vector pPIC-Zalpha his-topo (Invitrogen) using the following specific oligonucleotides:

SEQ ID NO. 21: Sense primer: GCGCCCCCGCCTAAC-CTC

SEQ ID NO. 22: Antisense primer: GTCGCTAGGCGT-CAGCAGCGA

Two saturated pre-cultures of 50 ml of BMGY medium (2% Peptone, 1% yeast extract, 1.34% YNB, 1% Glycerol, 100 mM potassium phosphate, 0.4 mg/Liter biotin pH 6.8) containing a clone coding for natural wild-type EPO or that coding for G104S EPO, were carried out for 24 hours at 30° C. at an agitation of 200 rotations per minute (rpm).

When the culture reaches a cellular density corresponding to an optical density of 5.0 measured at a wavelength of 600 nm, it is used to inoculate, at ⅕, 200 ml of BMMY medium (2% Peptone, 1% yeast extract, 1.34% YNB, 0.5% Methanol, 100 mM potassium phosphate, 0.4 mg/L biotin pH 6.8).

The expression of the protein is then induced by methanol at a final concentration of 0.5%, for 2 to 5 days at 30° C., with an agitation of the culture flask at 200 rpm.

The supernatant containing about 10 mg/ml of EPO-R is concentrated by ultra-filtration onto a labscale apparatus (cut-off 5000 Da) and buffer is exchanged by dialysis against sodium phosphate 50 mM, Tris(Cl) 10 mM, pH 8,0, NaCl 150 mM, imidazol 10 mM. Poly-histidine EPO-R is then captured onto a Hi-Trap pre-loaded with nickel-sulfate (Amersham Pharmacia). Fractions containing the protein were desalted using a gel filtration column (buffer Tris(Cl) pH 9, NaCl 50 mM) and then purified at about 95% onto an anionic exchange chromatography. Purity and concentration were estimated using SDS-PAGE gels.

The sensor chip NTA is then activated passing over nickel sulfate 500 μM with a flow of 20 μl/min. The EPO-R is then captured onto the surface at a concentration of 50 nM in a HBS-P buffer (10 mM HEPES, NaCl 150 mM, 0,005% P20 EDTA 50 μM) with a flow of 10 μl/min. Concentrations of wild-type EPO and G104S mutated EPO ranging from 0.45 to 15 nM were then passed over the sensor chip. A regeneration using HBS-P, EDTA 0.35M was performed after each concentration test. An automatic procedure permitted to evaluate the binding interaction of the wild-type EPO and G104S mutated EPO for the six concentrations in the range indicated above.

Figure 7:
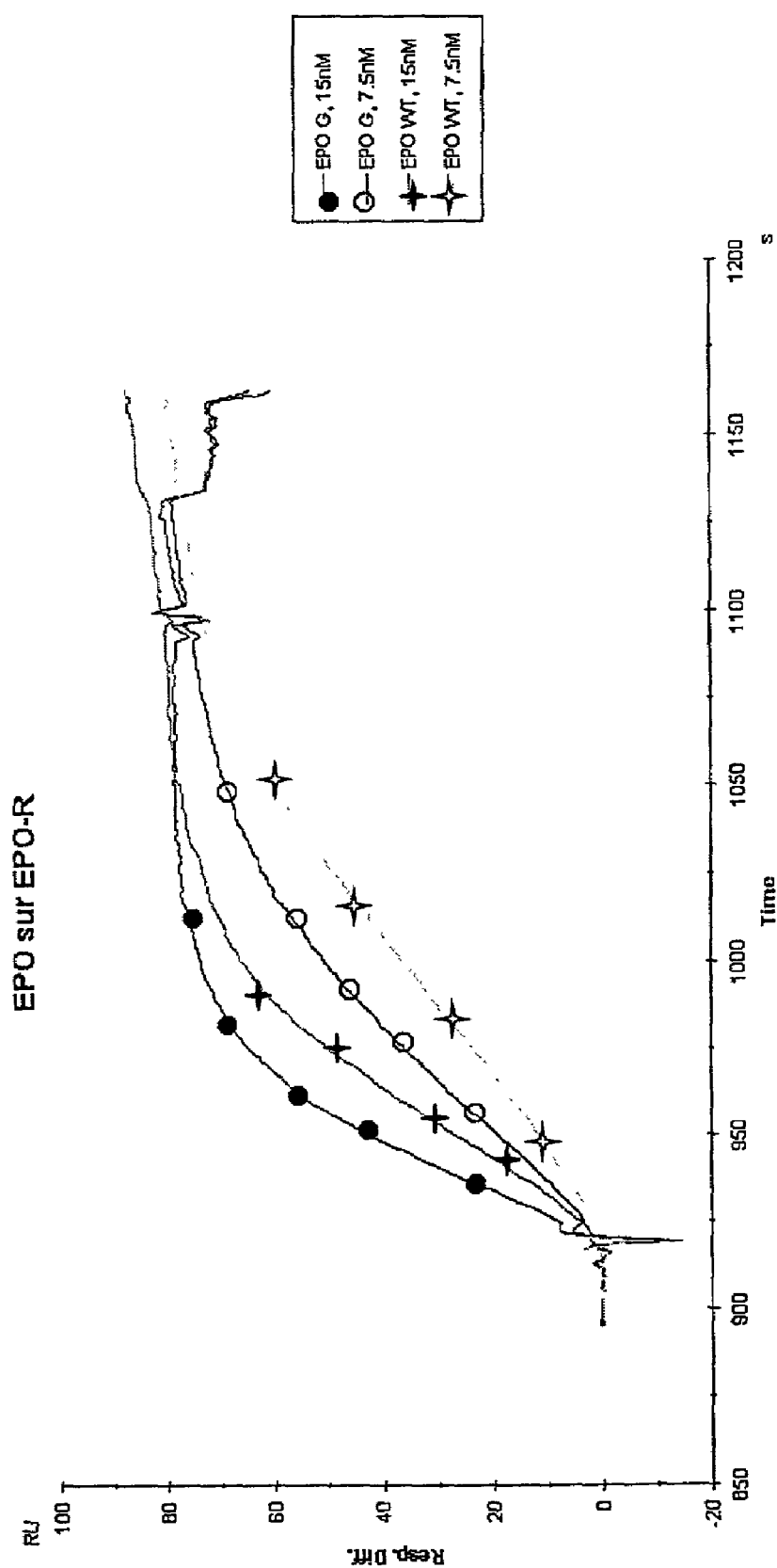
FIG. 7 represents the binding capacity of G104S mutated erythropoietin (circles) and wild-type erythropoietin (stars) to the external part of human EPO receptor. The data obtained with two concentrations of erythropoietin are represented: 7.5 nM in white, and 15 nM in black.

FIG. 7 shows the results of the binding measurements for two concentrations (7.5 and 15 nM) of G104S mutated EPO and wild-type EPO.

These results indicate that the G104S mutated EPO binds more quickly to its receptor than the wild-type EPO, confirming the effect observed at the cellular level (see examples described in 3f and 3g). As a consequence, this demonstrates that the strong positive effect of G104S mutated EPO on proliferation of murine 32D cells overexpressing the EPO receptor is related, at least in part, to a better affinity of G104S mutated EPO to its receptor.

This effect on EPO potency of a mutation affecting the amino acid at position 104 in the immature EPO protein sequence is extremely surprising. Indeed, the crystal structure of EPO complexed to the EPO receptor indicates that only the three helices A, C, and D of EPO (out of the four helices A, B, C, and D) are involved in the binding with EPO receptor (Syed et al. Efficiency of signaling through cytokine receptors depends critically on receptor orientation. Nature 395:511–516(1998)). In addition, site-directed mutagenesis analyzing the structure-function relationship in EPO demonstrates that changes in amino acids situated in helix B, in the neighborhood of residue 77, have no substantial effect on EPO activity (Eliott et al. Mapping of the active site of recombinant human erythropoietin. Blood. 89: 493–502 (1997); Wen et al. Erythropoietin structure-function relationships. Identification of functionally important domains. J. Biol. Chem. 269:22839–22846(1994)).

Such novel information on structure/function of EPO could also be used to identify, design and develop new EPO-like entities (either chemical or peptidic) that mimic EPO activity on its human receptor.

I claim:

1. An isolated polypeptide comprising amino acids 28 through 193 of the amino acid sequence SEQ ID NO. 2 and having SNP G104S.

2. A hyperglycosylated analog of an isolated polypeptide comprising amino acids 28 through 193 of the amino acid sequence SEQ ID NO. 2 and having SNP G104S.

3. An isolated polypeptide comprising an amino acid sequence having at least 95% identity with:

a) the amino acid sequence SEQ ID NO. 2; or b) amino acids 28 through 193 of the amino acid sequence SEQ ID NO. 2; wherein said polypeptide comprises the coding SNP G104S.

4. An hyperglycosylated analog of an isolated polypeptide of claim 3.

5. A therapeutic agent comprising a polypeptide of claim 3.

6. A therapeutic agent comprising a hyperglycosylated analog of claim 4.

* * * * *